(12) United States Patent
Abreu

(10) Patent No.: US 12,070,295 B2
(45) Date of Patent: Aug. 27, 2024

(54) SYSTEM AND METHOD FOR DETERMINING A SLEEP ONSET, SLEEP AROUSAL, AND SLEEP AWAKENING

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 330 days.

(21) Appl. No.: 16/584,987

(22) Filed: Sep. 27, 2019

(65) Prior Publication Data

US 2020/0100682 A1     Apr. 2, 2020

Related U.S. Application Data

(60) Provisional application No. 62/737,366, filed on Sep. 27, 2018.

(51) Int. Cl.
| | | |
|---|---|---|
| *A61B 5/01* | (2006.01) | |
| *A61B 5/00* | (2006.01) | |
| *A61B 5/0205* | (2006.01) | |
| *A61B 5/117* | (2016.01) | |
| *A61B 5/1455* | (2006.01) | |

(Continued)

(52) U.S. Cl.
CPC .............. *A61B 5/01* (2013.01); *A61B 5/0022* (2013.01); *A61B 5/742* (2013.01); *A61B 2562/0271* (2013.01)

(58) Field of Classification Search
CPC ........ A61B 2560/0412; A61B 2562/02; A61B 2562/0271; A61B 5/0008; A61B 5/0022; A61B 5/01; A61B 5/0205; A61B 5/02055; A61B 5/117; A61B 5/14553; A61B 5/369; A61B 5/4809; A61B 5/6803; A61B 5/681; A61B 5/6814; A61B 5/6821; A61B 5/6892; A61B 5/7275; A61B 5/742; G16H 50/00–50/80
See application file for complete search history.

(56) References Cited

U.S. PATENT DOCUMENTS

| | | |
|---|---|---|
| 7,187,960 B2 | 3/2007 | Abreu |
| 8,172,459 B2 | 5/2012 | Abreu |

(Continued)

*Primary Examiner* — Jonathan T Kuo
*Assistant Examiner* — Vynn V Huh
(74) *Attorney, Agent, or Firm* — Studebaker & Brackett PC

(57) ABSTRACT

Sleep enhancement system for assistance, monitoring, informing, and improving sleep habits of a user. A utilized monitoring device gathers user's vital signs for transmission to a smart device while an environment sensor gathers information from the surroundings which is then sent to an environment transmitter. Signals from the smart device and environment transmitter are transmitted to a processor by wireless transmission such as by electromagnetic waves, radio waves, infrared, sound or by being reported by audio or visual transmission. Signals are stored for current or future commands to control the environment, smart devices, and appliances for a user. In addition to being able to control these, an input to the ABTT terminus, such as heat or cold, can be applied to encourage entry into sleep or wake from sleep, as well as release of supplements or drugs through a patch placed on the ABTT terminus or another bodily region.

18 Claims, 12 Drawing Sheets

(51) Int. Cl.
    *A61B 5/369*     (2021.01)
    *G16H 50/30*     (2018.01)

(56) References Cited

U.S. PATENT DOCUMENTS

| | | |
|---|---|---|
| 8,328,420 B2 | 12/2012 | Abreu |
| 8,721,564 B2 | 5/2014 | Abreu |
| 8,849,379 B2 | 9/2014 | Abreu |
| 9,011,349 B2 | 4/2015 | Abreu |
| 9,119,530 B2 | 9/2015 | Abreu |
| 9,301,719 B2 | 4/2016 | Abreu |
| 9,408,572 B2 | 8/2016 | Abreu |
| 9,848,815 B2 | 12/2017 | Abreu |
| 10,123,732 B2 | 11/2018 | Abreu |
| 2006/0293608 A1* | 12/2006 | Rothman .............. A61M 21/00 368/9 |
| 2008/0157956 A1* | 7/2008 | Radivojevic ......... A61B 5/6887 700/12 |
| 2011/0125238 A1* | 5/2011 | Nofzinger ............. A61F 7/0085 607/109 |
| 2015/0094914 A1* | 4/2015 | Abreu ................ B60H 1/00742 701/41 |
| 2015/0105687 A1* | 4/2015 | Abreu ...................... A61F 7/00 600/549 |
| 2017/0124276 A1* | 5/2017 | Tee .................... G06F 21/6245 |

\* cited by examiner

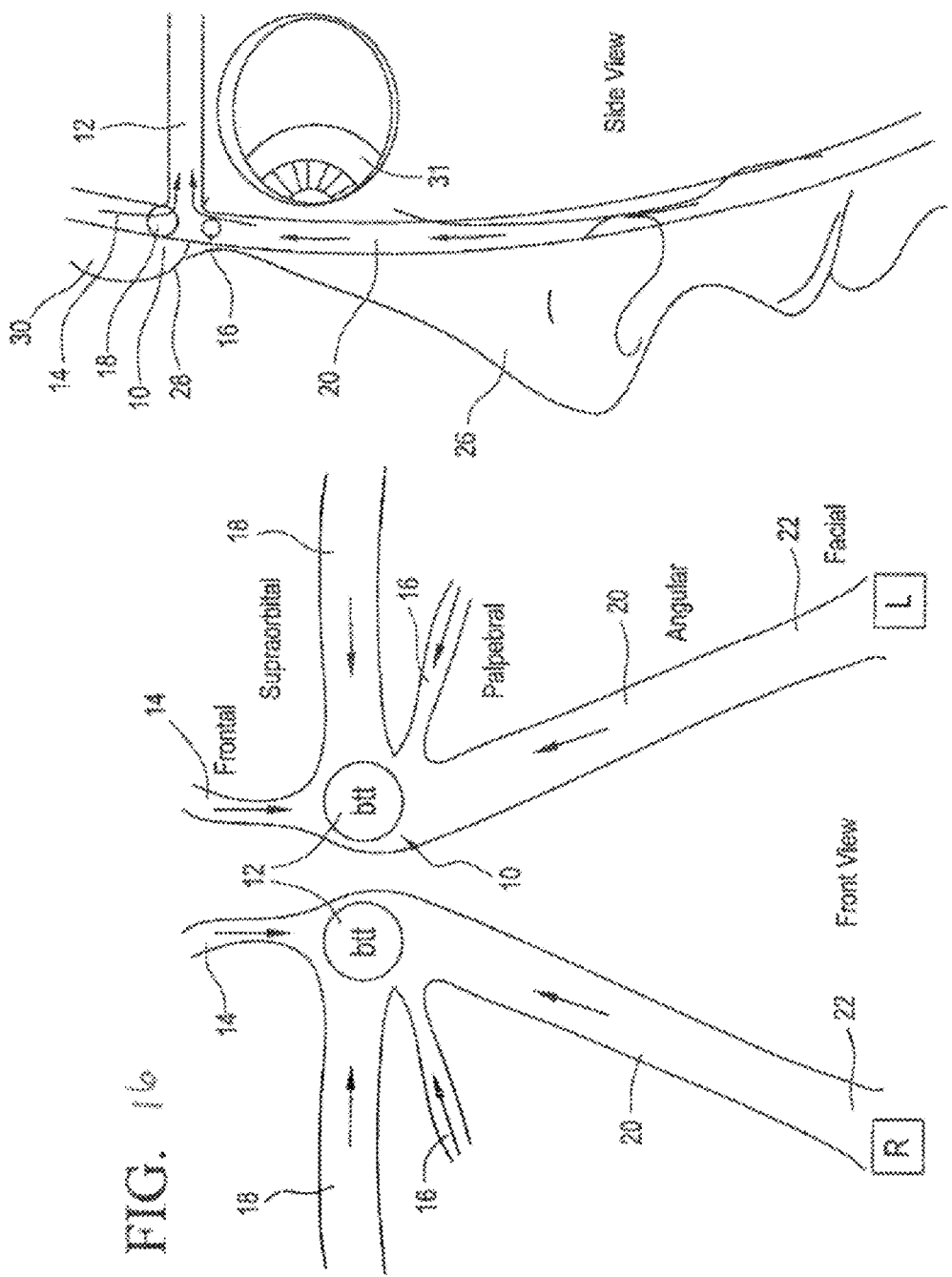

SYSTEM AND METHOD FOR DETERMINING A SLEEP ONSET, SLEEP AROUSAL, AND SLEEP AWAKENING

CROSS-REFERENCE TO RELATED APPLICATIONS

This application claims the benefit of priority to U.S. Provisional Patent Application No. 62/737,366, filed Sep. 27, 2018, which is hereby incorporated by reference in its entirety.

TECHNICAL FIELD

This disclosure generally relates to physiologic sleeping devices that assist, monitor, inform, and improve a user's sleeping habits.

BACKGROUND

Lack of sleep has been known for years as being a large factor in loss of productivity and preventable accidents. Many, if not all, of these accidents could be prevented by a system that helps a people get the required rest their body needs.

Sleep is merely just one step in the process for a body to get the rest it requires. Many people do go to a bed at a time when they can get sufficient rest, but simply can't fall asleep and stay asleep which causes a lack of sleep that results in loss of productivity and tiredness related accidents. There are many options for people, like medications, such as Melatonin to assist in falling asleep. All of these options are reliant on a drug that merely puts a person to sleep, but doesn't keep them asleep. Additionally, there are devices to monitor one's sleep, but diagnostics are all that a user can see. These monitoring devices do not help ensure a user stay asleep. Neither of these help a person prepare for sleep, maintain sleep or wake up in a subtle and non-abrupt way. They merely help a person go to sleep or monitor them.

Accordingly, it would be desirable to have a device and/or system that would not only help a person go to sleep, but get ready for sleep, maintain sleep, and wake from their sleep in a subtle manner The present invention provides a convergence between electronic products and the biological and anatomical aspects of the human body as well as the biomechanics of the human body while providing a series of hands-free and interchangeable wearable electronic apparatuses that can interact with human senses and physiology of the body in a practical manner. This specific invention would use the biological and anatomical aspects of the human body as well as the biomechanics of the body to assist a person in determining when to begin the pre-sleep process and when to begin sleeping. By doing this a person can get the required rest their body needs in order to stay productive and reduce the risk of preventable accidents due to lack of sleep. In addition to helping a person get ready for sleep and going to sleep, the electronic apparatuses being utilized in conjunction with the biological, anatomical, and biomechanics of the body help a person maintain their sleep by controlling a variety of parameters in the human body and the surrounding environment. By controlling these, a person is able to maintain a delta stage of sleep until the electronic devices begin to wake a person based on the readings from their biological, anatomical, and biomechanics.

There are a variety of ways to wake a person using electronics which are available today, but none rely on a convergence between electronic products and the biological and anatomical aspects of the human body and biomechanics of the body with a series of hands-free and interchangeable wearable electronic apparatuses that can interact with human senses and physiology of the body. By ignoring the biological, anatomical aspects, and biomechanics of the body, problems do, and often, arise. Abruptly being woken can lead to seizures and heart attacks for prone users. In addition to the problems previously stated, grogginess is another symptom of being woken abruptly from sleep which potentially leads a person to consume things detrimental to their health such as coffee and sugar. The desirable invention would help assist with all of these by not only focusing on pre-sleep, going to sleep, and maintaining sleep, but also subtly waking a person based on the readings of their body so that none of the problems stated above arise.

SUMMARY

This disclosure provides a system with the ability to identify a pre-sleep condition, comprising at least one monitoring device, such as, for example, a thermal monitor, a temperature monitor, an output monitor of the Abreu Brain Thermal Tunnel (ABTT) at an ABTT terminus that continuously and noninvasively measures a brain temperature signal, a heart monitor, an oxygen monitor, a galvanic skin monitor, a skin radiance monitor, a perspiration monitor, an electroencephalogram (EEG) monitor, and a multi-parameter monitor, an at least one smart device and appliance with a controller, at least one chemical sensor, at least one of an external ABTT processor and an internal ABTT processor, an at least one environment sensor, and an environment transmitter.

This disclosure provides a system to operate one or more systems to encourage transition from wakefulness to sleep of a user, comprising at least one monitoring device, such as a thermal monitor, a temperature monitor, an output monitor of the Abreu Brain Thermal Tunnel (ABTT) at an ABTT terminus that continuously and noninvasively measures a brain temperature signal, a heart monitor, an oxygen monitor, a galvanic skin monitor, a skin radiance monitor, a perspiration monitor, an electroencephalogram (EEG) monitor, and a multi-parameter monitor, an at least one smart device and appliance with a controller, at least one chemical sensor, at least one of an external ABTT processor and an internal ABTT processor, an at least one environment sensor, and an environment transmitter.

This disclosure provides a system to monitor and maintain sleep of the user, and to awaken the user, comprising at least one monitoring device, such as a thermal monitor, a temperature monitor, an output monitor of the Abreu Brain Thermal Tunnel (ABTT) at an ABTT terminus that continuously and noninvasively measures a brain temperature signal, a heart monitor, an oxygen monitor, a galvanic skin monitor, a skin radiance monitor, a perspiration monitor, an electroencephalogram (EEG) monitor, and a multi-parameter monitor, an at least one smart device and appliance with a controller, at least one chemical sensor, at least one of an external ABTT processor and an internal ABTT processor, an at least one environment sensor, and an environment transmitter.

This disclosure provides a system to identify pre-sleep conditions, identify and assist in wakefulness to sleep, monitor and maintain sleep as well as additionally monitoring the temperature of ABTT terminus with an ABTT temperature sensor with the ability to provide a heat to, and remove a heat from, the ABTT terminus comprising a monitoring device and a temperature modification device.

The system can also provide detection and treatment of harmful diseases, such as hyperthermia, which can be an indication of cold, flu, infection, etc.; identification of shark fin temperature curves, which is an indication of undesirable shark fin temperature curve sleep; and identification of hypothermia, which can include thermal patterns that can be an indication of Alzheimer's disease and/or more serious issues, including body core temperature issues that can lead to death. Shark fin temperature rise is undesirable. The system tries to suppress/limit rise of temperature to prevent a shark fin temperature curve. Potential benefits of the system are gathered in the form of data from populations, which can be used to further refine temperature ranges and curves that are indicative of disease and/or conditions. The device can find optimum time for sleep, which is often difficult as people are unable to detect the optimum physiologic time to sleep.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 16 shows a simplified partial cross-sectional view through a human skull in a vertical direction showing an ABTT and certain other facial features.

FIG. 17 shows a view of s stylized representation of flow of blood into a brain core.

DETAILED DESCRIPTION

Figure 18:
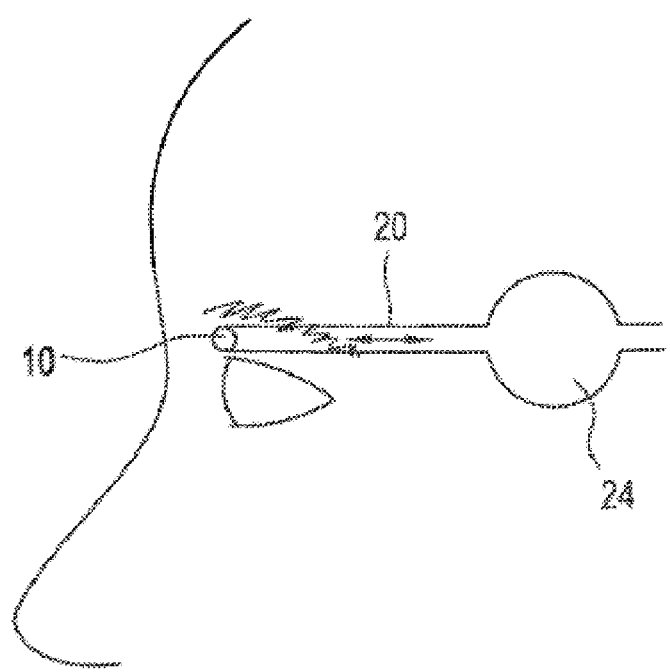
FIG. 18 shows a view of the route of the ABTT terminus to the brain core.

The present disclosure arises from the discovery that the Abreu Brain Thermal Tunnel (ABTT) provides the first known structure for a brain-surface thermodynamic communication and a thermal connection directly with the center of a brain. Anatomically and physiologically speaking, and as shown in FIGS. 16-18, ABTT 12 includes a continuous, direct, and undisturbed connection between a brain core 24 at a control center of the brain and skin of the ABTT terminus 10. The skin of the ABTT terminus 10 is unique in that it is the thinnest skin on the human body with an absent fat layer. This allows for the highest thermal conductivity of any skin on the human body.

The physical and physiological events at one end of a first ABTT tunnel are reproduced at the end of a second ABTT tunnel. The ABTT 12 enables a direct transfer of outputs from the brain core 24 to the ABTT terminus 10 without significant barriers, as described in co-pending U.S. patent application Ser. No. 14/512,421, filed on Oct. 11, 2014, the '421 application hereinafter, incorporated by reference herein in its entirety. Accordingly, the present disclosure describes apparatuses, systems, devices, mechanisms, and methods that use the ABTT terminus 10 and the ABTT 12 to measure the temperature of the brain core 24.

Anatomy shows the convergence of four veins at the ABTT terminus 10: a frontal 14, a superior palpebral 16, a supraorbital 18, and an angular 20. As the angular vein 20 extends further from the ABTT 12, it transitions into the facial vein 22. After converging, blood from the four veins flows toward the brain core 24 from the ABTT terminus 10 between an eye 31 and an eyebrow into the center of the brain. This is the temperature center present in a hypothalamus or a thermal storage area of the body, which is positioned in a cavernous sinus. From the thermal storage area, blood is distributed throughout a plurality of brain tissues and the body, and may be used to effectively and efficiently treat and/or prevent medical conditions by the transmission of a plurality of medications, chemicals, and compounds to the brain.

The disclosed sleep enhancement system includes the ability to identify a pre-sleep condition, to operate one or more systems to encourage transition from wakefulness to sleep of a user, to monitor and maintain sleep of the user, and to awaken the user. Such system can be configured to perform such operations based on optimal transition into delta sleep based on monitoring an Abreu brain thermal tunnel (ABTT) 12 with an Abreu Brain Thermal Tunnel (ABTT) temperature sensor 303, electroencephalogram (EEG), and enzymes, such as a cortisol level test/monitoring, and a melatonin level test/monitoring, separately or in any combination, to determine optimum sleep onset, sleep arousal, and sleep awakening times.

The disclosed system includes a device to monitor the condition of sleep and to enter a sleep-facilitating mode. As disclosed hereinabove, the device is a monitoring device in part, and a controlling processor in part. The device is part of a system that monitors optimal sleep patterns to provide several benefits. First, the device and the system are able to determine an optimum time to sleep. When a pre-sleep pattern is identified, at least one of an external ABTT processor which can be any processor not connected to a device that a user is directly using and an internal ABTT processor which can be any processor that is a part of a device that a user is in direct control of, takes control of a smart device to assist in an environmental transition from wakefulness to sleep, principally by the control of an electronics device and an environment. The at least one smart device 115 and appliance 101 work by accepting a user's vital sign signals then transmitting them by way of an at least one smart device signal an appliance signal then accepting a command from said at least one external ABTT processor and internal ABTT processor 102 by way of a controller contained within. However, the device and the system can also provide an input to the ABTT terminus 10 to encourage entry into sleep or wake from sleep. The physical and chemical parameters measured by the ABTT temperature sensor 303 to assist in determining input to the ABTT terminus 10 include brain function, metabolic function, hydrodynamic function, hydration status, levels of chemical compounds in the blood, and the like.

Such smart device 115 able to accept a user's vital signs and transmit a smart device signal can include, for example, a tablet, a computer, a watch 1310, a clock 401, a facemask, a pair of glasses 801, a chest band 1403, a waist band 1404, an ABTT signal receiver portal, an interactive pillow, an interactive blanket, an interactive frame, an interactive mattress, an interactive sheet, wrist bands 1202, goggles 1120, a sport helmet, a combat helmet, a headset, an ABTT patch, and the like. All of these smart devices 115 have capabilities to be wired or wireless. Additionally, all of the smart devices can be equipped notification sensors 305 in the form of an LED light containing a library of colored alerts for a user to view, a vibration code containing a library of patterned alerts for a user to feel without removing any smart device from something such as a pocket, and a display screen to display a library of textual alerts for a user to read. The library of textual alerts contains a plurality of suggested actions for the user to take based upon determination of any given reference values. These can be, for example, to take medication, sit down, lay down, put phone down, eat, drink, and the like. The display screen additionally has wireless capabilities to send the library of textual alerts to an external screen away from the smart device for a user to read if away from all other smart devices. This external screen could be a computer, a screen in a vehicle, or the like. The ABTT signal receiver portal is a standalone device the user does not carry on their person. The said signal receiver portal receives vital signs from at least one of the monitoring devices, then sends a smart device signal to the at least one external ABTT processor and internal ABTT processor 102. The interactive pillow, interactive mattress, interactive blanket, interactive sheets, and interactive frame can all take actions with a command from the at least one external and internal processor. These can include, but are not limited to, for example, heating up, cooling down, changing firmness, raising or lowering, changing an angle, vibration, and the like. The ABTT patch can be any type of patch placed on the ABTT terminus 10 of a user. This patch has the ability to read the ABTT as well as administer a wide variety of supplement and/or drugs to any part of the body and these supplements and/or drugs can include, but are not limited to, for example, melatonin, ADHD medicine, anti-depressants, testosterone, essential body vitamins, caffeine, and the like.

Such appliance able to accept a user's vital signs and transmit a smart device signal can include, for example, a coffee maker, a stove, an oven, a toaster oven, a hot tub, an automatic bathtub, a garage door, a fridge, a reclining chair, a cleaning robot, a vehicle, and the like. These appliances and all like ones are things in a user's everyday life that help them do things. For example, when said at least one external ABTT processor and internal ABTT processor 102 send a command to said at least one smart device 115, an additional command can be sent to an appliance like a coffee maker. When the at least one external ABTT processor and internal ABTT processor 102 determines it's time for a user to awake, it can send a command to make coffee while awaking the user. Additional commands can be taken as well, such as, but not limited to, starting a heater in a vehicle, running the bath water to heat it up, and the like. These controlled appliances 101 just assist a user in making their everyday lives easier and more proficient.

Such monitoring device able to gather vital signs of a user and transmit to a smart device 115 or appliance 101 can include, for example, a thermal monitor 110, a temperature monitor 111, an output monitor of the Abreu Brain Thermal Tunnel (ABTT) 103 at an ABTT terminus 10 that continuously and noninvasively measures a brain temperature signal, a heart monitor, an oxygen monitor, a galvanic skin monitor, a skin radiance monitor, a perspiration monitor, an electroencephalogram (EEG) monitor, and a multi-parameter monitor 112. These all monitor different parts of the human physiology and gather a plurality of vital signs critical in determining sleep onset and sleep awakening. The multi-parameter monitor 112, for example, can gather more than one vital sign at a time which could be, for example, heart rate and oxygen, which are two things needed to determine optimal sleep onset and sleep awakening.

Upon determining that body conditions are on track to lead to a sleep condition, which can be identified from the continuous and noninvasive reading of a brain temperature signal at the ABTT terminus 10, as well as vital signs gathered from a monitoring device like a multi-parameter monitor, the at least one external ABTT processor and internal ABTT processor 102 begin interacting with the at least one smart device 115 and an at least one environment sensor. The at least one external ABTT processor and internal ABTT processor 102 consists of a memory and a processing circuit wherein a plurality of reference values from an at least one smart device signal and appliance signal and a plurality of environment data points are stored for a commands to be sent to a controller contained in the at least one smart device 115 and appliance 101. The at least one external ABTT processor and internal ABTT processor 102 works in conjunction with the smart device 115 and at least one environment sensor. Signals received are transmitted to the at least one external ABTT processor or internal ABTT processor 102 by wireless transmission such as by electromagnetic waves, radio waves, infrared, sound and the like or by being reported locally by audio or visual transmission. The at least one environment sensor continuously gathers a plurality of environment data points which are captured and stored by an environment transmitter to send out while at the same time the smart device 115 continuously and noninvasively gathers a plurality of smart device signals from a plurality of vital signs, which can include, but are not limited to, conductance of the skin, heart rate, oxygen levels, blood pressure, and respiratory rate, body movement, body sounds, body position, brain temperature, and the like. The environment data points are sent by the environment transmitter to the at least one external ABTT processor and internal ABTT processor 102 which is configured to analyze the plurality of environment data points gathered from the surroundings as well as the input of the at least one smart device signal and appliance signal gathered from the at least one smart device 115 and appliance 101 that receive a user's vital signs. Once this data is analyzed the at least one external ABTT processor and internal ABTT processor 102 can take control of the surroundings and a plurality of user conditions based off the reference values and suggested actions. These reference values can be real time, or from the past, for example, from a week or two weeks prior. The reference values stored in a memory for storing of the at least one external ABTT processor and internal ABTT processor 102 and a predictive action can be taken based off a user's habits to create an ideal surrounding for a user by sending a command to a controller in a smart device 115 or appliance 101 before a command would normally be sent based of a user's vital signs. There is also the ability to directly affect a user by way of, for example, directly inducing supplement/drugs through patches, including at ABTT or any other sites of the body, such as for example, a leg, an arm, a stomach, a hand, a foot, and the like, heating or cooling the ABTT terminus 10. Additionally, in conjunction with controlling the environment and user conditions, an alert will be sent via a smart device 115 by way of at least one of a LED light, a vibration code, and a display screen. The user additionally has the option to activate a safety alert feature that can send alerts if abnormalities or serious conditions are detected. If activated, and a user's conditions do not change or worsen after the at least one external ABTT processor and internal ABTT processor 102 takes a plurality of counter actions, a second alert can be sent via internet connection, a landline, or a wireless communication device to a police station, a relative, a doctor, a pharmacy, a hospital, or the like.

The at least one external ABTT processor and internal ABTT processor 102 can control things such as, for example, closing of blinds, closing of curtains, activating or de-activating at least one audio device, activating or de-activating a smart device 115 or appliance 101, including, but not limited to, a interactive pillow temperature, an interactive mattress temperature, an interactive blanket temperature, an interactive sheet temperature, an interactive mattress firmness, an interactive blanket firmness, a bed angle, a bed position, activate an HVAC system for heating or cooling 316, emit a fragrance 310, activate an air humidifier or dehumidifier 306, activate and air purifier, activate a dispenser with essential oils, ceiling fans, jets in a bathtub or hot tub, activate a vibration pad 904, activate a pollutant minimizer, and if windows can be electronically controlled to decrease light transmission, adjusting the transmission of light through windows to decrease as much as possible or to completely block light transmission. Control of external light entering an internal environment is in conjunction with control of internal lighting, which can be dimmed in communal areas, such as a living room, a family room, a kitchen, etc., and increased in areas leading to sleeping area, such as a hallway. Such control of lighting may include change in a frequency from an awake frequency to a yellow or a blue light to encourage slowing a brain activity in preparation for sleep.

In addition to controlling the above, the at least one external ABTT processor and internal ABTT processor 102 can control a plurality of individual electronics, particularly a smart device 115 or appliance 101, by way of, for example, a Wi-Fi connection or a Bluetooth connection. Such control can be gradual, by informing the user that a television will be shut down in a certain number of minutes, or at a certain time. For the smart device 115 or appliance 101, each one of the devices can include its own warning, and can be sequenced based on the user desire. For example, a videogame and the television can be shut down first, after a warning. Next, for example, a communication device, such as a tablet and a cellphone, can be transitioned to a "do not disturb" user sleep mode, which can be configured to permit a plurality of emergency calls from an individual. Next, for example, a laptop and a computing device can be controlled by the at least one external ABTT processor and internal ABTT processor 102 to begin a controlled shutdown, with automatic save of open documents and warnings to any person in receipt of an active communication from the computing device that the device is in an automatic shutdown mode.

A factor that can affect entry into sleep, as well as remaining in sleep, is ambient or environmental temperature. Thermal receptors, principally in the feet and hands, can affect core and or brain temperature because the brain considers these receptors as an indication of environmental conditions that require compensation. For example, if the thermal receptors in the hands or feet indicate cool or cold temperatures, the brain, and more specifically the hypothalamus, warm the brain to prevent what the brain believes is a potential hypothermic condition. Accordingly, control of environmental temperature, such as by way of an HVAC system 316, electrically operated blanket and the like, can be valuable in averting excessive brain warming leading to awakening. It should be similarly apparent from the disclosure herein that preventing excessive brain cooling reduces the risk of a life-threatening hypothermic condition.

In addition to leading to sleep, cooling the brain during sleep promotes healing in the brain of cumulative damage, as well as removal of toxins that build up while awake. When the brain operates at a cooler temperature for an insufficient length of time, healing and toxin removal can be insufficient for long-term brain health, which can ultimately exacerbate or lead to conditions such as Alzheimer's disease. Accordingly, the system and apparatus of the present disclosure help maintain a decreased body core and brain temperature. One approach to maintaining cooler core and brain temperature is to prevent thermal receptors in the extremities, i.e., the hands and feet, from sending signals to the brain that the body core and brain must be warmed. Accordingly, the system and apparatus of the present disclosure can control the HVAC or other heating/cooling system to increase temperature after the initial transition from wakefulness to sleep.

As an example, if the time from wakening or being awake to sleep is two hours, after the two hour, or other cool down interval, the HVAC 316 or other heating/cooling system is operated to increase the temperature of the room. Increasing the temperature of the room causes heating of thermal receptors in the extremities, leading the hypothalamus to believe that the body is experiencing an undesirable increase in temperature, which cause the hypothalamus to cool the brain or keep the brain at a current cool temperature rather than increasing brain temperature. As the temperature of the ABTT terminus 10 is monitored, and the at least one external ABTT processor and internal ABTT processor 102 analyzes the brain temperature, the at least one external ABTT processor and internal ABTT processor 102 can determine that an environmental or an ambient temperature should be increased. Further, throughout the course of a single night's sleep, the environmental temperature may need to be adjusted to be higher or lower than an existing temperature to maintain an optimal sleep temperature in the ranges discussed elsewhere herein.

In an exemplary embodiment, the at least one external ABTT processor and internal ABTT processor 102 can also be configured to control an audio system 104, which can include changing the music from, for example, a progressive rock to a style of slow, mellow music to encourage pulse rates and brain activity to decrease. The at least one external ABTT processor and internal ABTT processor 102 will then completely shut down a communal area lighting, as well as access to the electronics, and then begin to dim a plurality of transition areas, such as the hallway, with the goal of encouraging the user to move toward a bathroom and then to a bedroom. If the at least one external ABTT processor and internal ABTT processor 102 does not detect operation of certain appliances, such as, for example, an electric toothbrush, the at least one external ABTT processor and internal ABTT processor 102 can begin to provide warnings that may need to be manually shut off, such as an alert, an alarm, or a warning in a bathroom area to encourage the user to move to the bathroom area. As part of sleep-facilitating, the at least one external ABTT processor and internal ABTT processor 102 can then transition an area such as the bathroom to a sleep mode, encouraging the user to move to a sleeping area, such as a bedroom.

In the bedroom, the at least one external ABTT processor and internal ABTT processor can play asleep-appropriate music, provide white noise, or other sounds that the at least one external ABTT processor and internal ABTT processor has identified as being conducive to sleep, or that the user or a resident has identified as being conducive to sleep. The bed can include a smart thermally controllable blanket or pad that provides an optimum temperature for sleep based on a plurality of sensor readouts, including the ABTT tunnel 12 readouts. The at least one external ABTT processor and internal ABTT processor is able to turn off various systems that might otherwise awaken the user, such as a cellphone, an alarm clock, a doorbell, etc. The system can be programmed to permit specific interruptions, such as a call from a boss, a police station, a significant other, etc.

The at least one external ABTT processor and internal ABTT processor 102 can also be configured to monitor a sleep condition, as well as a pre-arousal condition, and take steps to prevent awakening if such awakening is before an optimal awakening time, which can be determined from the ABTT terminus 10 temperature. Such steps can include modifying a bed temperature to be higher or lower to warm or cool the resident. This is typically by tenths of a degree in order to optimize body temperature for sleep. Other steps can include engaging or modifying music, white noise, sound, e.g., rain or wind sounds, to be conducive to returning to deeper sleep from an arousal state.

A factor that can affect entry into sleep, as well as remaining in sleep, is ambient or environmental temperature. Thermal receptors, principally in the feet and hands, can affect core and or brain temperature because the brain considers these receptors as an indication of environmental conditions that require compensation. For example, if the thermal receptors in the hands or feet indicate cool or cold temperatures, the brain, and more specifically the hypothalamus, warm the brain to prevent what the brain believes is a potential hypothermic condition. Accordingly, control of environmental temperature, such as by way of an HVAC system 316, electrically operated blanket and the like, can be valuable in averting excessive brain warming leading to awakening. It should be similarly apparent from the disclosure herein that preventing excessive brain cooling reduces the risk of a life-threatening hypothermic condition.

In addition to leading to sleep, cooling the brain during sleep promotes healing in the brain of cumulative damage, as well as removal of toxins that build up while awake. When the brain operates at a cooler temperature for an insufficient length of time, healing and toxin removal can be insufficient for long-term brain health, which can ultimately exacerbate or lead to conditions such as Alzheimer's disease. Accordingly, the system and apparatus of the present disclosure help maintain a decreased body core and brain temperature. One approach to maintaining cooler core and brain temperature is to prevent thermal receptors in the extremities, i.e., the hands and feet, from sending signals to the brain that the body core and brain must be warmed. Accordingly, the system and apparatus of the present disclosure can control the HVAC 316 or other heating/cooling system to increase temperature after the initial transition from wakefulness to sleep.

As an example, if the time from wakening or being awake to sleep is two hours, after the two hour, or other cool down interval, the HVAC 316 or other heating/cooling system is operated to increase the temperature of the room. Increasing the temperature of the room causes heating of thermal receptors in the extremities, leading the hypothalamus to believe that the body is experiencing an undesirable increase in temperature, which cause the hypothalamus to cool the brain or keep the brain at a current cool temperature rather than increasing brain temperature. As the temperature of the ABTT terminus 10 is monitored, and the at least one external ABTT processor and internal ABTT processor 102 analyzes the brain temperature, the at least one external ABTT processor and internal ABTT processor 102 can determine that an environmental or an ambient temperature should be increased. Further, throughout the course of a single night's sleep, the environmental temperature may need to be adjusted to be higher or lower than an existing temperature to maintain an optimal sleep temperature in the ranges discussed elsewhere herein.

The at least one external ABTT processor and internal ABTT processor 102 is also able to determine an optimum time to awaken, again based on temperature. During the awakening process, various systems are operated to encourage the user or resident to wake up. Such systems can include modifying temperature of the bed, engaging or increasing lights, changing audio system 104 from being sleep conducive to an awake-facilitating mode. Appliances, such as a coffee maker, can be engaged, along with an HVAC system to encourage odors to transfer to the bedroom and/or bathroom of the user. A television can also be automatically turned on to, for example, news, and other electronic devices can be engaged. In addition, windows can be opened to permit external light to enter. Though the description provided above can affect the entire household, it should be noted that individuals can have their own smart device 115, and the at least one external ABTT processor and internal ABTT processor 102 can be programmed to minimize effects on residents with different awakening/sleeping times, to the extent such interference is able to be eliminated.

The device can monitor the Abreu brain thermal tunnel (ABTT) 12 by way of an ABTT temperature sensor 303, electroencephalogram (EEG), and enzymes that can be monitored, such as cortisol, and melatonin, separately or in any combination, to determine optimum sleep time and awaken times. These functions can be part of a sleep service. Enzyme levels are important for determining best sleeping and waking times. Enzymes can be monitored by way of a contact lens with sensor, by way of saliva, and/or by way of perspiration or sweat.

While optimal sleep patterns are preferred for longevity and health, in some circumstances, a human must awaken rapidly. For example, a fireman might need to awaken quickly to respond to a fire. A soldier might need to awaken quickly to respond to an attack or intruders. A parent might need to awaken quickly to attend to a child. However, rapid wakening leads to elevated adrenaline, rapidly increased pulse rate, rapid temperature rise, and other physiological effects. These effects are the direct result of the action of the hypothalamus. While these effects may have been beneficial in many circumstances, the stress they cause upon the body can lead to strokes and heart attacks. Accordingly, one embodiment of the present disclosure provides a system to reduce the negative effects of rapid wakening. To reduce the negative effects of rapid wakening, an embodiment of the present disclosure can engage a plurality of systems to speed awakening while controlling core body temperature by way of the ABTT terminus 10. It should be noted that core body temperature can also be measured at the same location, as disclosed in more detail hereinbelow.

It would additionally be desirable to have a visual pattern recognition device included. The device would consist of a camera including infrared camera capabilities to capture images that would be used in conjunction with said at least one external ABTT processor and internal ABTT processor for determining activities performed by the individual such as drinking water, taking a pill, getting out bed, getting in bed, moving around/sleep walking, or any other activity.

It should be apparent that one significant benefit of the systems and methods of the present disclosure is controlling a change in temperature per time; i.e., a delta T per unit time. Furthermore, by changing the delta T as appropriate to the awakening stage, temperature overshoot and adrenaline production can be suppressed, reducing stress on internal organs that lead to damage and failure.

Figure 1:
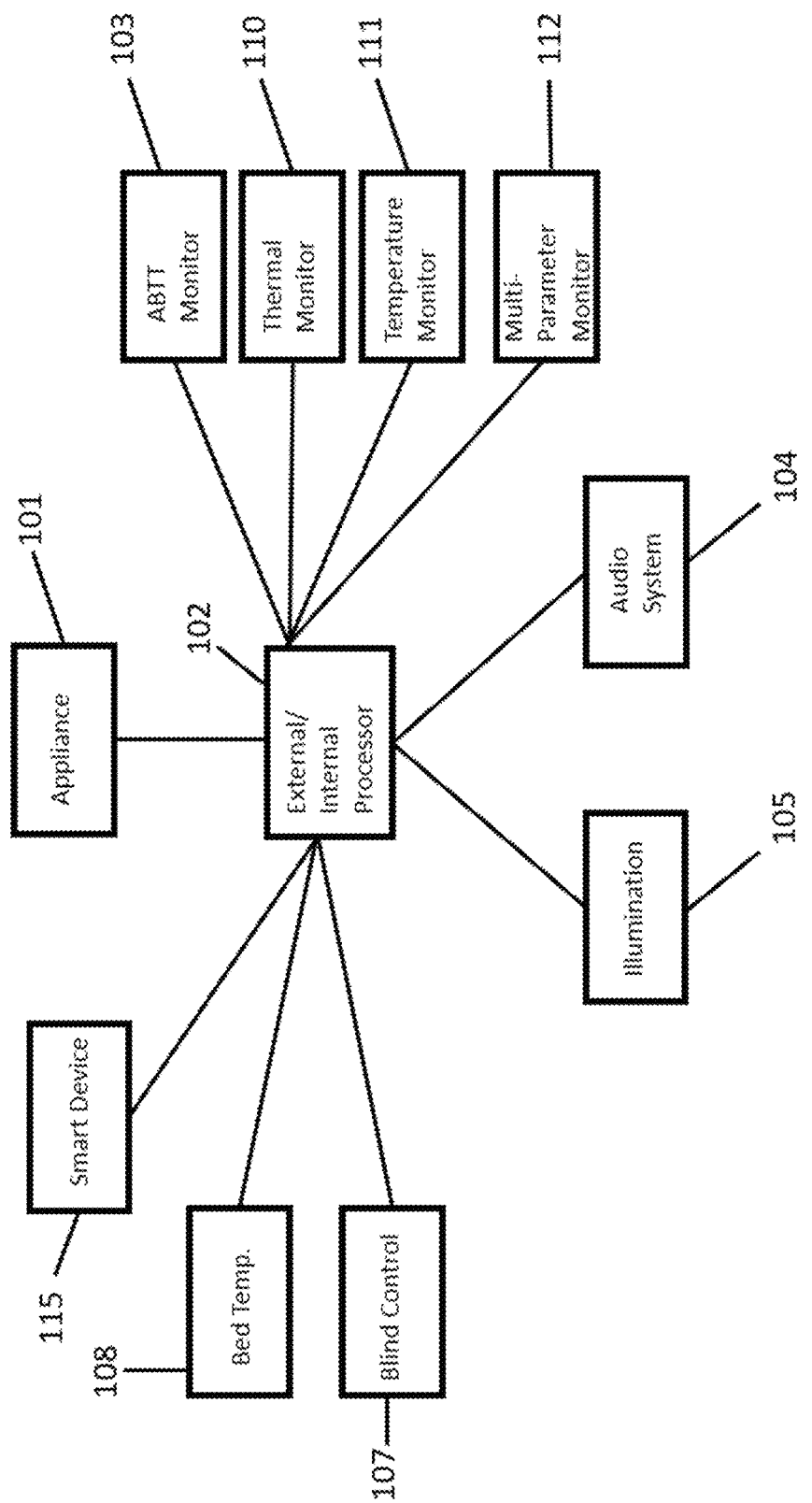
FIG. 1 is a block diagram of the sleep facilitating, maintaining, and waking system showing how external and internal ABTT at least one external ABTT processor and internal ABTT processor works with a plurality of electronic devices, monitors, and appliances and to assist a user in optimal sleep by activating a variety of features.

FIG. 1 shows a wakening system that includes a plurality of monitoring devices, ABTT monitor 103, a thermal monitor 110, a temperature monitor 111, and a multi-parameter monitor 112 that monitor one or more conditions of the human body. The ABTT monitor is monitored at the ABTT terminus 10 which has been disclosed by Applicant in various patents and applications under the title "Apparatus and Method for Measuring Biologic Parameters," including U.S. Pat. No. 7,187,960, issued Mar. 6, 2007, U.S. Pat. No. 8,172,459, issued May 8, 2012, U.S. Pat. No. 8,328,420, issued Dec. 11, 2012, U.S. Pat. No. 8,721,562, issued May 13, 2014, U.S. Pat. No. 8,849,379, issued Sep. 30, 2014, U.S. Pat. No. 9,011,349, issued Apr. 21, 2015, U.S. Pat. No. 9,119,530, issued Sep. 1, 2015, U.S. Pat. No. 9,848,815 B2, issued Dec. 26, 2017, U.S. Pat. No. 10,123,732 B2, issued Nov. 13, 2018, U.S. Pat. No. 9,301,719 B2, issued Apr. 5, 2016, and U.S. Pat. No. 9,408,572 B2, issued Aug. 9, 2016, the contents of which are incorporated by reference in their entirety herein. The plurality of monitoring devices, ABTT monitor 103, a thermal monitor 110, a temperature monitor 111, and a multi-parameter monitor 112, can monitor blood analytes, electrical currents, sweat, and blood enzymes. The monitoring devices, ABTT monitor 103, a thermal monitor 110, a temperature monitor 111, and a multi-parameter monitor 112, are connected to an at least one external ABTT processor and internal ABTT processor 102. The at least one external ABTT processor and internal ABTT processor 102 can be co-located with the plurality of monitoring devices, ABTT monitor 103, a thermal monitor 110, a temperature monitor 111, and a multi-parameter monitor 112, or can be separate. The wakening system can be configured to perform such operations based on optimal insertion into delta sleep based on monitoring the Abreu brain thermal tunnel (ABTT) 12, and enzymes, such as cortisol, and melatonin, separately or in any combination, to determine optimum sleep time and awaken times.

The wakening system can include the at least one external ABTT processor and internal ABTT processor 102 that receives a plurality of inputs and provides a plurality of outputs to control various systems. Broadly, the at least one external ABTT processor and internal ABTT processor 102 can control a plurality of environmental systems by outputting a plurality of control signals. The at least one external ABTT processor and internal ABTT processor 102 receives inputs from at least one of a first ABTT monitor 103, a thermal monitor 110, and a temperature monitor 110, and the like to provide a gradual wakening to avoid the negative physiological as described herein. Additionally, the at least one external ABTT processor and internal ABTT processor 102 can control a plurality of environmental sub-systems that can work in conjunction. The controlled sub-systems can include an audio system 104, a bed temperature modification device 108, a window control device 107, an electronic device control 106, a light system 105, and one or more appliances 101.

The audio system 104 can include a digital audio media stored in a non-transitory memory, a radio, a tape player, a CD, and a DVD. The window control device 107 can include an automatic drape, an automatic blind, an electrically actuated window tint, and the like. The smart device 115 and appliance 101 can control a plurality of smart devices 115 and appliances 101, including a tablet, a laptop, a PDA, a video game system, a television, a watch, a clock, a pair of glasses, an ABTT receiving portal which is separated from all other smart devices, a coffee maker, a stove, an oven, a toaster oven, a hot tub, an automatic bathtub, a garage door, a vehicle, and the like. The bed temperature control system 108 can include an interactive pillow, an interactive mattress, an interactive frame, and interactive, sheet, an interactive blanket, a heating pad, and other systems for controlling the temperature of a bed or other sleeping location, which can include a cot, an inflatable mattress, a couch, an Asian-style floor pad, and the like.

Figure 2:
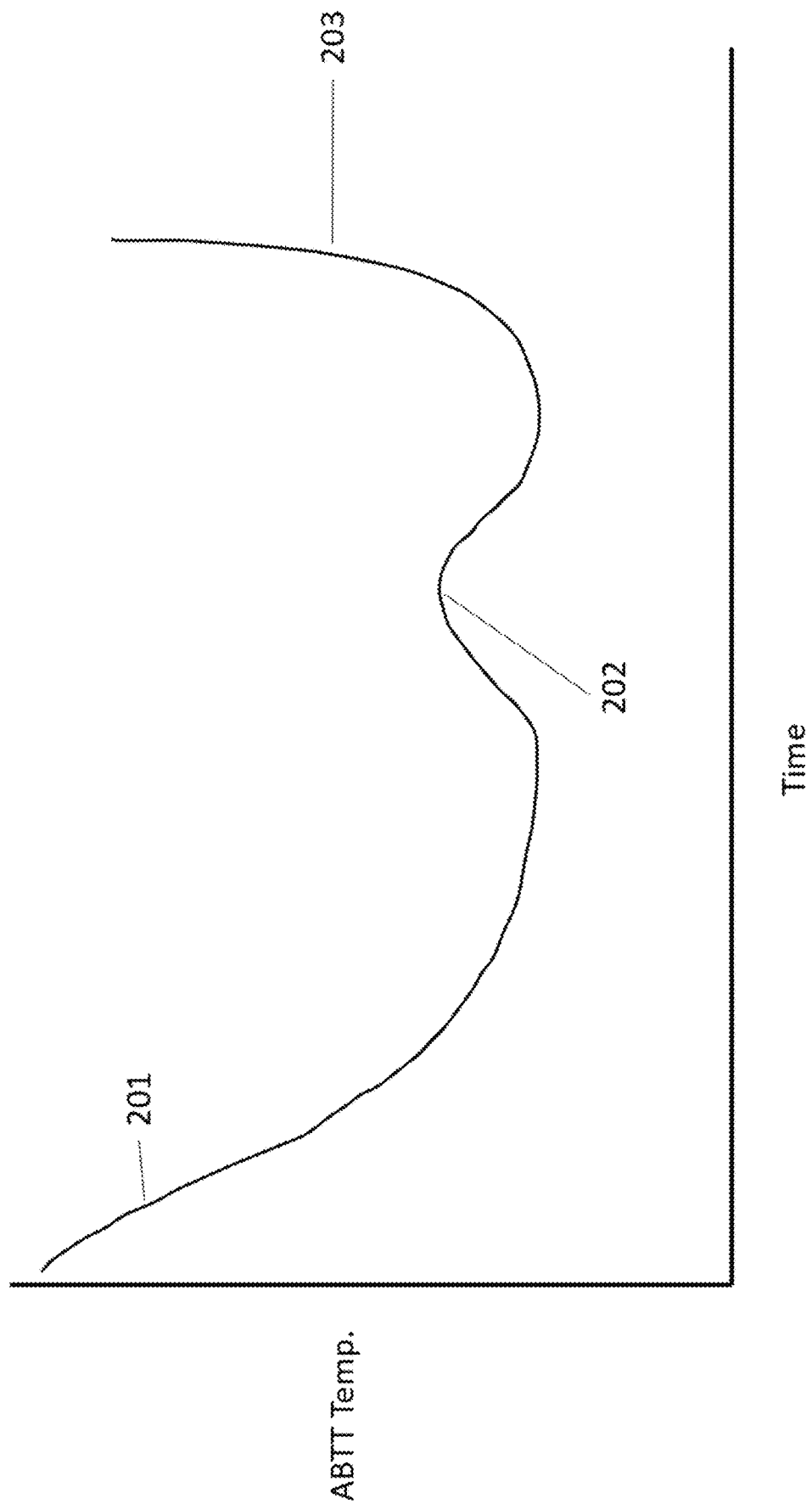
FIG. 2 is a pre-sleep and during sleep arousal and awakening pattern with demonstration of the undesirable "sharkfin".

FIG. 2 shows the at least one external ABTT processor and internal ABTT processor 102 identifying a pre-sleep pattern which includes the sleep time pattern 201, undesirable shark fin 202, and awakening pattern 203. Identification of the pre-sleep pattern can be entirely based on a temperature measured by an ABTT temperature sensor 303 at the ABTT terminus 10, or can be based in part on temperature measured at the ABTT terminus 10, augmented by readings from sweat, blood analytes, electrical body currents, and a plurality of chemical sensors. The chemical sensors can include, for example, amperometric sensors, blood analyte substance sensors, parametric sensors, fluorescent sensors, optical sensors, and the like. If a sleep pattern is optimally followed, the sleep pattern ultimately leads to entry into a delta wave sleep, which Applicant has found to be an optimal sleep mode for health and longevity. However, many people deny entry into an optimal sleep pattern by taking steps to remain awake, which include interaction with a plurality of electronic devices such as a television, a computing device, a communication device, video game devices, etc. The at least one external ABTT processor and internal ABTT processor 102 overcomes the tendency of people to remain awake by operating devices, including powering down devices, to enforce entry into a sleep pattern that leads to the delta wave sleep.

Figure 3:
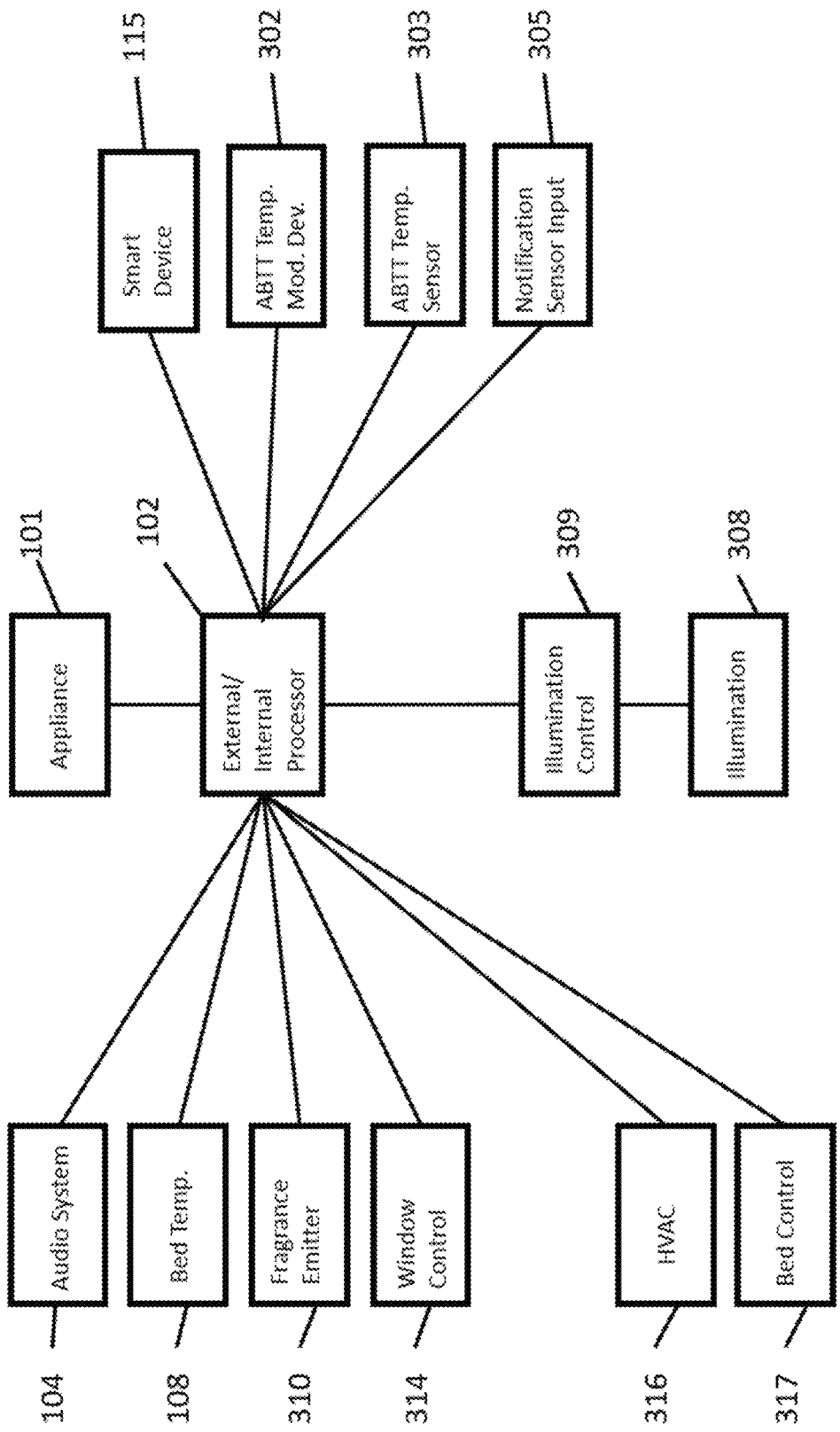
FIG. 3 is a block diagram of the sleep facilitating, maintaining, and waking system with the ability to heat and cool by way of the ABTT of a user.

FIG. 3 shows a wakening system that includes an at least one external ABTT processor and internal ABTT processor 102 that receives a plurality of inputs and provides a plurality of outputs to control a plurality of systems. Broadly, the at least one external ABTT processor and internal ABTT processor 102 can control a plurality of environmental systems and at least one body temperature modification device 302 by outputting control signals. The at least one external ABTT processor and internal ABTT processor 102 receives inputs from an ABTT temperature sensors 303 to provide a gradual wakening to avoid the negative physiological described herein. The at least one external ABTT processor and internal ABTT processor 102 can control a plurality of environmental sub-systems that can work in conjunction. The controlled sub-systems can include an audio system 104, a bed temperature modification device 108, a window control device 314, an HVAC system 316, a bed control system 317, a fragrance emitter 310, one or more appliances 101, a smart device 115, and one or more illumination devices 308 that can be controlled by way of an illumination control device 309.

The audio system 104 can include digital audio media stored in a non-transitory memory, a radio, a tape player, a CD, and a DVD. The bed temperature modification device 108 can include an electric blanket, a heating pad, and other systems for controlling the temperature of a bed or other sleeping location, which can include a cot, an inflatable mattress, a couch, an Asian-style floor pad, and the like. The window control device 314 can include an automatic drape, an automatic blind, an electrically actuated window tint, and the like. The smart device 115 and appliance 101 can control and be a plurality of devices, including a tablet, a coffee maker, a stove, an oven, a toaster oven, a hot tub, an automatic bathtub, a laptop, a PDA, a video game system, a television, a watch, a clock, a pair of glasses, an ABTT receiving portal which is separated from all other smart devices, a tablet, a computer, a watch, a clock, a facemask, a pair of glasses, a chest band, a waist band, an interactive pillow, an interactive blanket, an interactive frame, an interactive mattress, an interactive sheet, a sport helmet, a combat helmet, a headset, an ABTT patch, and the like. The HVAC system 316 can include a whole house heating system, a whole house air conditioning system, a room heating system, a room air conditioning system, a fan, a swamp cooler, and other temperature modification devices. The bed control system 317 can include a bed vibration system, a bed raising and lowering system via an interactive frame that is configured to mechanically adjust the position of a mattress, an interactive pillow to control firmness, an interactive mattress to control firmness, an interactive sheet, an interactive blanket, and the like. The fragrance emitter 310 can include any system for emitting an odor associated with waking, that can include an acrid odor, such as that associated with coffee, a cooking odor, an unpleasant odor, and the like. The illumination control device 308 can include a dimmer, an on/off switch, and other light control devices that can turn illumination devices on and off or vary the intensity of the illumination devices.

The at least one external ABTT processor and internal ABTT processor 102 can receive inputs from one or more smart device 115 and/or appliance 101. Notification sensors 305 then send an alert to a user on smart device 115 or appliance 101. Such sensors can include an alarm input, a sound or noise input, such as sensing a baby crying, a gun firing, a window breaking, an alarm sound, or other noises that might be associated with an urgent need to awaken, an input from a carbon monoxide sensor, and the like. The at least one external ABTT processor and internal ABTT processor 102 can also be connected to a head-mounted device that combines an ABTT temperature sensor 303 and an ABTT temperature modification device 102. In passive operation, the at least one external ABTT processor and internal ABTT processor 102 receives temperature data from one or both ABTT temperature sensors 303. The at least one external ABTT processor and internal ABTT processor 102 can then modify the temperature of one or both ABTT terminuses 10 by actuating a temperature modification device 302 for a predetermined period, followed by a predetermined period of cool down, after which the temperature sensor can acquire ABTT terminus 10 temperature data. In active operation, the at least one external ABTT processor and internal ABTT processor 102 can use baseline ABTT terminus 10 temperature data as a starting point for controlling temperature of the ABTT temperature to prevent temperature spiking during waking.

It should be understood that during portions of an optimal sleep cycle, body core temperature should be hypothermic. Such hypothermic sleep is beneficial in that it helps remove brain toxins by expanding interstitial spaces between nerves. By receiving temperature measurements from one ABTT terminus 10, and applying heat or cooling to the other ABTT terminus 10, or by alternating operation of temperature sensors 303 and temperature modification devices 302 such as thermoelectric devices, an optimal hypothermic sleep state can be achieved that is sufficiently low to induce enhanced sleep while avoiding an excessive hypothermic state that might inhibit enzyme functions.

Under normal waking circumstances, the system of FIG. 3 is configured to begin a gradual waking process that can begin, for example, approximately 30 minutes before a desired awakening time. The gradual process can include gradually increasing light from one or more illumination devices 308, providing initially gentle bed vibrations or repositioning a mattress, changing room temperature, engaging audio systems 104 increasing light input into the room from one or more windows, modifying room fragrances, engaging one or more appliances 101 and smart devices 115, and the like. The at least one external ABTT processor and internal ABTT processor 102 can also actuate one or both ABTT temperature modification devices 302 to change core body temperature, typically by increasing core body temperature by a controlled amount. The at least one external ABTT processor and internal ABTT processor 102 is able to monitor the effect of engaging various sub-systems by monitoring the temperature of at least one ABTT terminus 10, or by disengaging one or both ABTT temperature sensors 303 and engaging one or both ABTT temperature modification devices 302, followed by a cool down interval, after which the temperature of one or both ABTT terminuses 10 is measured again. Such carefully controlled awakening leads to minimal brain and body stress, helping to maintain the beneficial effects of optimal sleep.

In a situation where a lengthy, gradual awakening is not possible, the system of FIG. 3 is configured to provide a rapid awakening without an excessive, potentially damaging temperature spike and adrenaline rush initiated by the hypothalamus that can lead to heart attack and stroke. One or more environmental subsystems can be engaged for rapid awakening, only with a significantly shorter time period, such as one minute or less, thirty seconds or less, or, in extreme cases, five seconds or less. However, the at least one external ABTT processor and internal ABTT processor 102 immediately engages the ABTT temperature modification devices 302 and controls temperature at one or both ABTT terminuses 10 based on ABTT terminus 10 temperature immediately before the need to awaken is determined.

For example, a sensor input can determine a baby is crying. While urgent, the at least one external ABTT processor and internal ABTT processor 102 recognizes that awakening can be, for example, over a period of a minute. The at least one external ABTT processor and internal ABTT processor 102 immediately engages or actuates the ABTT temperature modification devices 302 to input heat to one or both ABTT terminuses 10 to a level that can be in the range of 34 to 37 degrees Celsius in an exemplary embodiment. In another embodiment, the input temperature can be in the range of 35 to 36 degrees Celsius. In a situation where the baseline temperature of the ABTT terminus is 34 degrees Celsius, the at least one external ABTT processor and internal ABTT processor 102 can initiate a controlled temperature rise of 1 degree Celsius over the course of 60 seconds, which cause the hypothalamus to release enzymes and hormones to cause awakening. However, the temperature input at the ABTT terminus 10 can be maintained below a predetermined maximum temperature, such as 36 degrees Celsius, by operation of the ABTT temperature modification devices 302 to prevent the hypothalamus from releasing excessive sympathetic adrenaline in an excessive hyperthermic state, reducing the risk of high heart rate and blood pressure that can lead to stroke and heart attack. In essence, the system of FIG. 3 modifies the slope of the temperature rise rate in the brain core, thus modifying the function of the hypothalamus, i.e., tricking the hypothalamus, in a beneficial way to reduce awakening trauma. Even in a circumstance where awakening needs to be extremely short, such as five seconds, the system of FIG. 3 can effectively make use of all five seconds to control the temperature rise rate of the brain core. However, the faster awakening, the greater the amount of adrenaline. Thus, the goal is to suppress the angle of the slope to the angle permitted by the awakening interval, which decreases adrenaline release.

Figure 4:
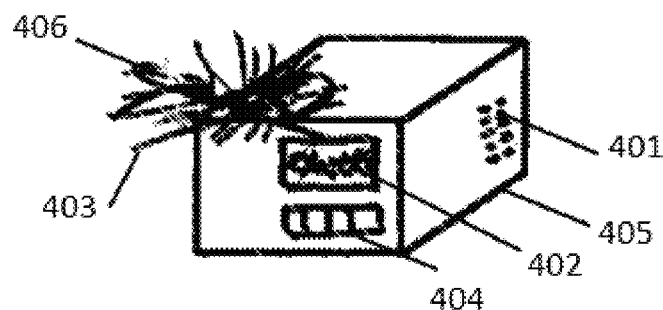
FIG. 4 shows a view of an exemplary embodiment a clock equipped with a spray/mist device.

FIG. 4 shows an implementation of the system of FIG. 3 in accordance with an exemplary embodiment of the present disclosure. In this implementation, the at least one external ABTT processor and internal ABTT processor 102 is located within a clock 401 with a time display screen 402 and a plurality of control buttons 404 on the front. The clock includes a spray or mist device 403 for spraying or misting fluid 404. In use, the clock is positioned to direct the sprayed or misted fluid 404 in the direction of the user. At a predetermined period before a waking time, the clock actuates the mister or sprayer 403 to output or emit a gentle mist or spray 406 to begin a waking process. This embodiment relies upon a predetermined sleep curve and the set time on the alarm clock to begin the waking process rather than a temperature input from the user.

Figure 5:
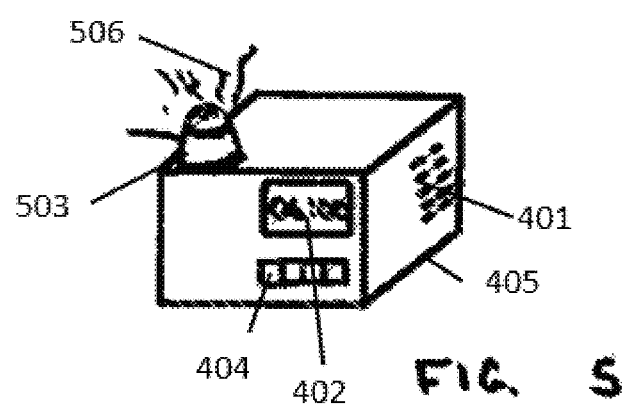
FIG. 5 shows a view of an exemplary embodiment a clock equipped with a fragrance device.

FIG. 5 shows an implementation of the system of FIG. 3 in accordance with another exemplary embodiment of the present disclosure. In this implementation, the at least one external ABTT processor and internal ABTT processor 102 is located within a clock 401 with a time display screen 402 and a plurality of control buttons 404 on the front. The clock includes a fragrance device 503 to emit an odor 504. In use, the clock is positioned to position the fragrance device 503 in a region or location near a sleeping user. At a predetermined period before a waking time, the clock actuates the fragrance device 503 to output or emit an odor 506 to begin a waking process. This embodiment relies upon a predetermined sleep curve and the set time on the alarm clock to begin the waking process rather than a temperature input from the user.

Figure 6:
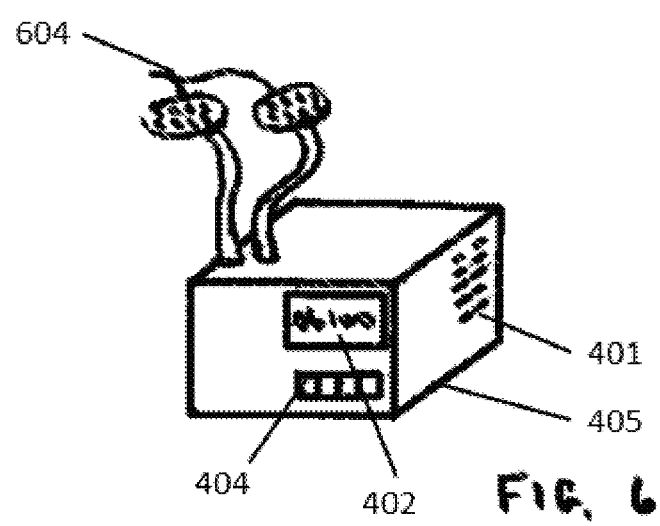
FIG. 6 shows a view of an exemplary embodiment of a clock equipped with an illumination device.

FIG. 6 shows an implementation of the system of FIG. 3 in accordance with yet another exemplary embodiment of the present disclosure. In this implementation, the at least one external ABTT processor and internal ABTT processor 102 is located within a clock 401 with a time display screen 402 and a plurality of control buttons 404 on the front. The clock includes one or more illumination devices 604, such as an LED. In use, the illumination device or devices are positioned to shine in the direction of a sleeping user. At a predetermined period before a waking time, the clock actuates the illumination device(s) 604, which can initially be a very low intensity, to begin a waking process. This embodiment relies upon a predetermined sleep curve and the set time on the alarm clock to begin the waking process rather than a temperature input from the user. In this case, the rate at which the light is intensified is varied depending on the predetermined sleep curve, as disclosed in more detail hereinbelow.

Figure 7:
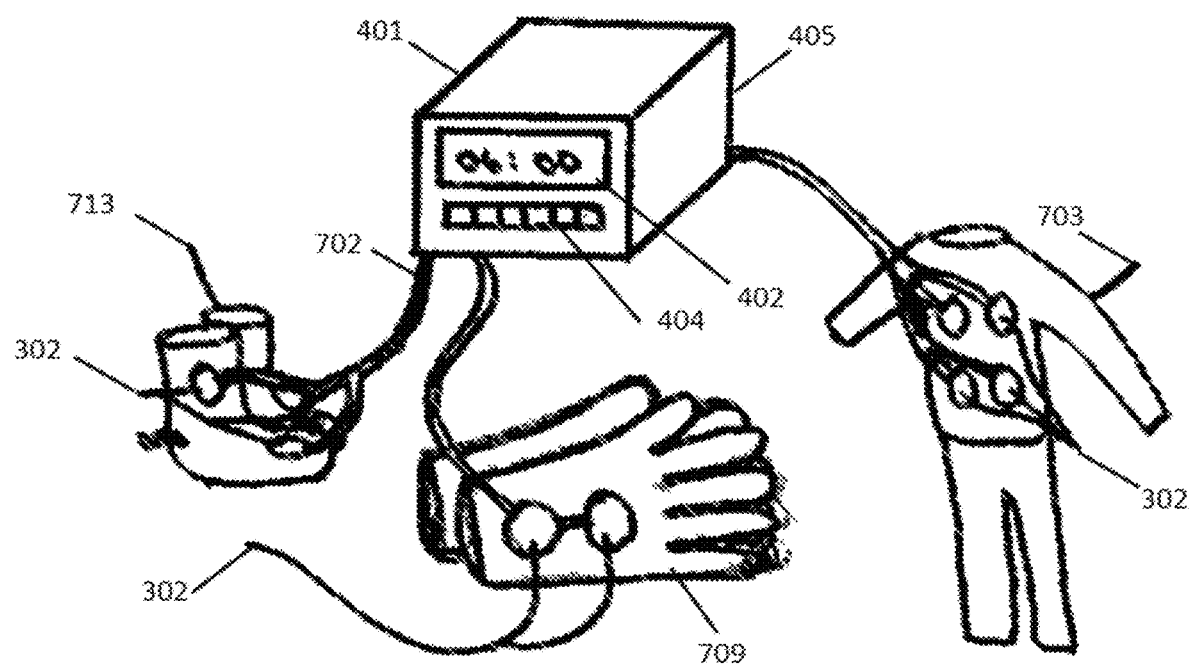
FIG. 7 shows a view of an exemplary embodiment of a clock attached to a glove, a sock, and/or a pajama set.

FIG. 7 shows an implementation of the system of FIG. 3 in accordance with yet another exemplary embodiment of the present disclosure. In this implementation, the at least one external ABTT processor and internal ABTT processor 102 is located within a clock 401 with a time display screen 402 and a plurality of control buttons 404 on the front. The clock is connected by wires or cables 702 to vibration devices and/or temperature modification devices 706 positioned on or in one or more of socks 713, gloves 709, pajamas 703, or other wearable articles. In use, at a predetermined period before a waking time, the clock actuates the temperature modification devices 302 to gradually stimulate a waking process. This embodiment relies upon a predetermined sleep curve and the set time on the alarm clock to begin the waking process rather than a temperature input from the user.

Figure 8:
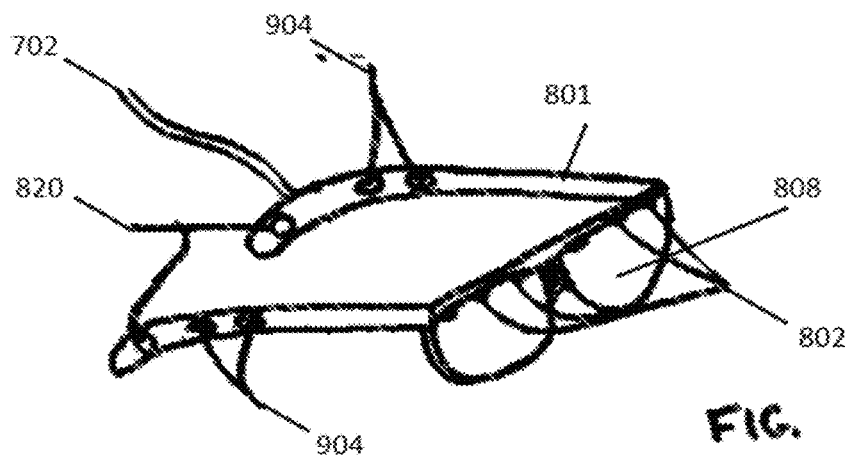
FIG. 8 shows a view of an exemplary embodiment of a pair of glasses with vibration devices, lights, and audio output.

FIG. 8 shows an implementation of the system of FIG. 3 in accordance with still yet another exemplary embodiment of the present disclosure. In this implementation, the at least one external ABTT processor and internal ABTT processor 102 is located within a clock 401. The clock is connected by wires or cables 702 to eyeglasses or eyeglass frames 810 with eyeglass lenses 808. The eyeglasses or eyeglass frames 801 can include illumination devices 802, e.g., light emitting diode (LED) lights, audio output, and vibration devices. In use, at a predetermined period before a waking time, the clock actuates one or more of the illumination devices, audio output 820, and vibration devices 904 to gradually stimulate a waking process. This embodiment relies upon a predetermined sleep curve and the set time on the alarm clock 401 to begin the waking process rather than a temperature input from the user.

Figure 9:
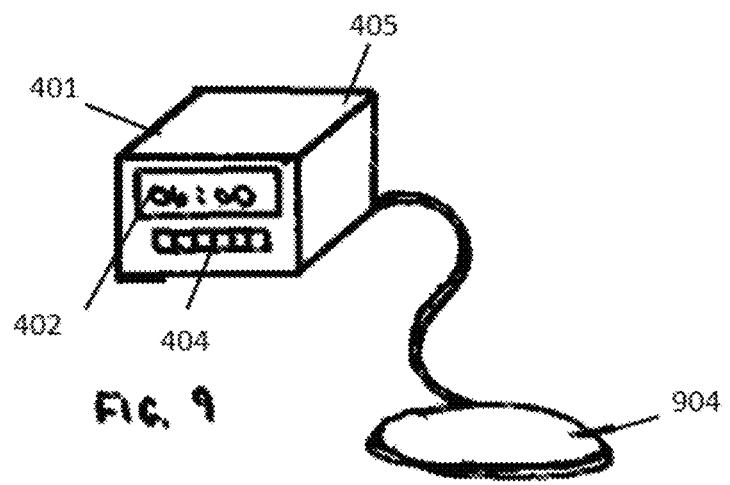
FIG. 9 shows a view of an exemplary embodiment of a clock connected to a vibration device.

FIG. 9 shows an implementation of the system of FIG. 3 in accordance with a further exemplary embodiment of the present disclosure. In this implementation, the at least one external ABTT processor and internal ABTT processor 102 is located within a clock 401 with a time display screen 402 and a plurality of control buttons 404 on the front. The clock 401 is connected by wires or cables 702 to a vibration device 904 that the user can sleep on or with. In use, at a predetermined period before a waking time, the clock actuates the vibration device 904 to gradually stimulate a waking process. This embodiment relies upon a predetermined sleep curve and the set time on the alarm clock to begin the waking process rather than a temperature input from the user.

Figure 10:
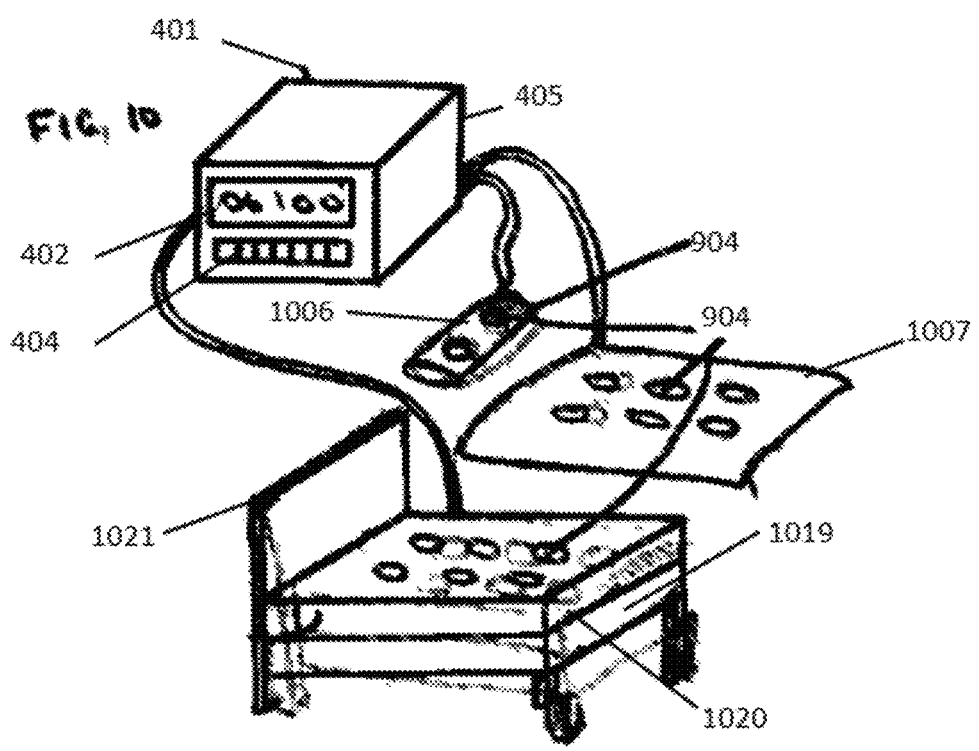
FIG. 10 shows a view of an exemplary embodiment of a clock connected to pieces of a bed.

FIG. 10 an implementation of the system of FIG. 3 in accordance with a further exemplary embodiment of the present disclosure. In this implementation, the at least one external ABTT processor and internal ABTT processor 102 is located within a clock 401 with a time display 402 and a plurality of control buttons 404 on the front. The clock 401 is connected by wires or cable 702 that the user can sleep with to a vibration device 904 which can be on a pillow 1006, a mattress pad or sheet 1007, or a mattress 1020 that sits on top of a box 1019 which is on a bed frame 1021. In use, at a predetermined period before a waking time, the clock actuates the vibration device 904 to gradually stimulate a waking process. This embodiment relies upon a predetermined sleep curve and the set time on the alarm clock to begin the waking process rather than a temperature input from the user.

Figure 11:
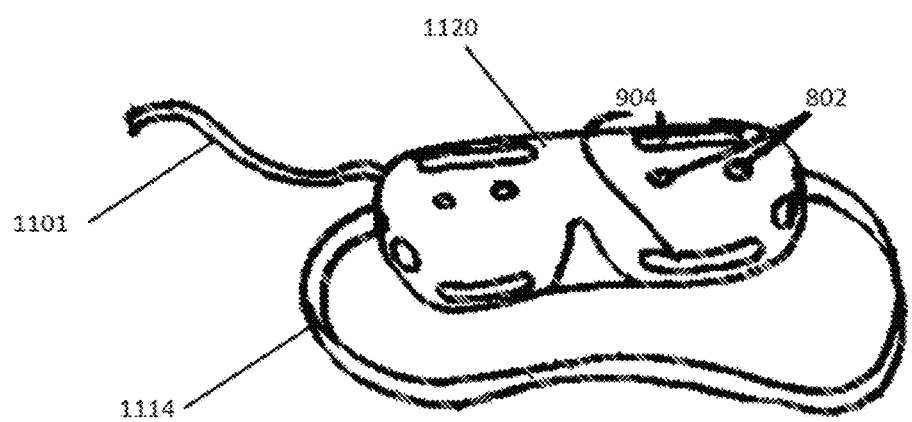
FIG. 11 shows a view of an exemplary embodiment of a face mask with vibration devices and lights.

FIG. 11 shows an implementation of the system of FIG. 3 in accordance with still yet another exemplary embodiment of the present disclosure. In this implementation, the at least one external ABTT processor and internal ABTT processor 102 is located within a clock 401. The clock is connected by wires or cables 702 to a face mask 1120 with a head band 1114. The face mask 1120 can include lights 802 and/or vibration devices 904. In use, at a predetermined period before a waking time, the clock actuates one or more of the illumination devices and vibration devices to gradually stimulate a waking process. This embodiment relies upon a predetermined sleep curve and the set time on the alarm clock to begin the waking process rather than a temperature input from the user.

Figure 12:
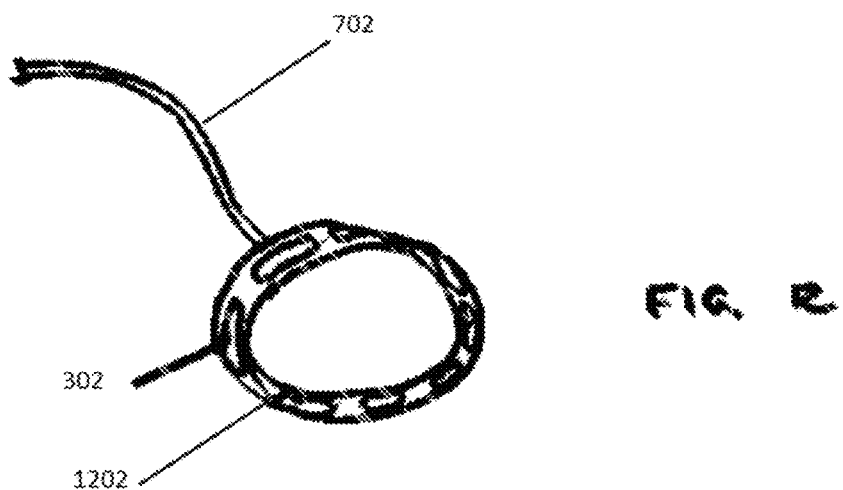
FIG. 12 shows a view of an exemplary embodiment of a wrist band with temperature modification devices.

FIG. 12 shows an implementation of the system of FIG. 3 in accordance with still yet another exemplary embodiment of the present disclosure. In this implementation, the at least one external ABTT processor and internal ABTT processor 102 is located within a clock 401. The clock is connected by wires or cables 702 to a wrist band 1203. The wrist band 1203 can include temperature modification devices 302. In use, at a predetermined period before a waking time, the clock actuates one or more of the temperature modification devices 302 to gradually stimulate a waking process. This embodiment relies upon a predetermined sleep curve and the set time on the alarm clock 401 to begin the waking process rather than a temperature input from the user.

Figure 13:
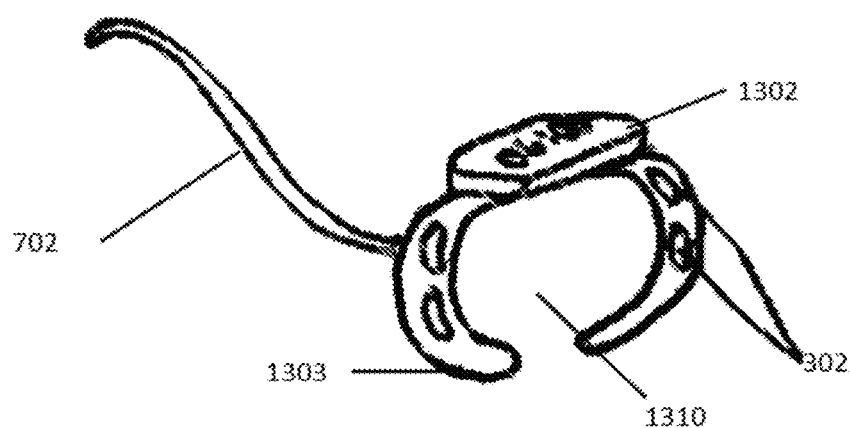
FIG. 13 shows a view of an exemplary embodiment of a watch with temperature modification devices.

FIG. 13 shows an implementation of the system of FIG. 3 in accordance with a further exemplary embodiment of the present disclosure. In this implementation, the at least one external ABTT processor and internal ABTT processor 102 is located within a clock 401. The clock is connected by wires or cables 702 to a watch 1310 that includes one or more temperature modification devices 302. The watch includes a display 1302 and a band 1303. In use, at a predetermined period before a waking time, the clock actuates one or more of the temperature modification devices to gradually stimulate a waking process. This embodiment relies upon a predetermined sleep curve and the set time on the alarm clock to begin the waking process rather than a temperature input from the user.

Figure 14:
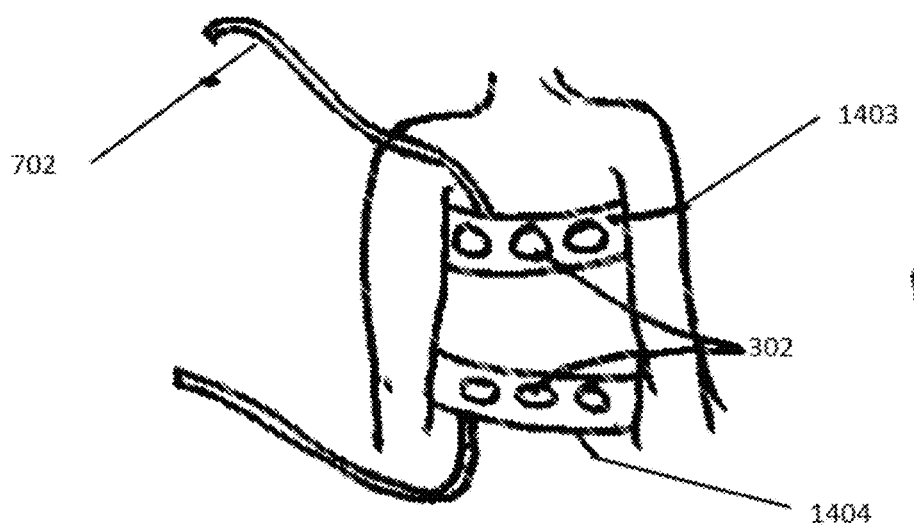
FIG. 14 shows a view of an exemplary embodiment of a chest band and waist band device with temperature modification devices.

FIG. 14 shows an implementation of the system of FIG. 3 in accordance with even further exemplary embodiments of the present disclosure. In this implementation, the at least one external ABTT processor and internal ABTT processor 102 is located within a clock 401. The clock 401 is connected by wires or cables 702 to one or more of a chest band 1403 and a waist band 1404, each of which includes one or more temperature modification devices 302. In use, at a predetermined period before a waking time, the clock 401 actuates one or more of the temperature modification devices 302 to gradually stimulate a waking process. This embodiment relies upon a predetermined sleep curve and the set time on the alarm clock to begin the waking process rather than a temperature input from the user.

Figure 15:
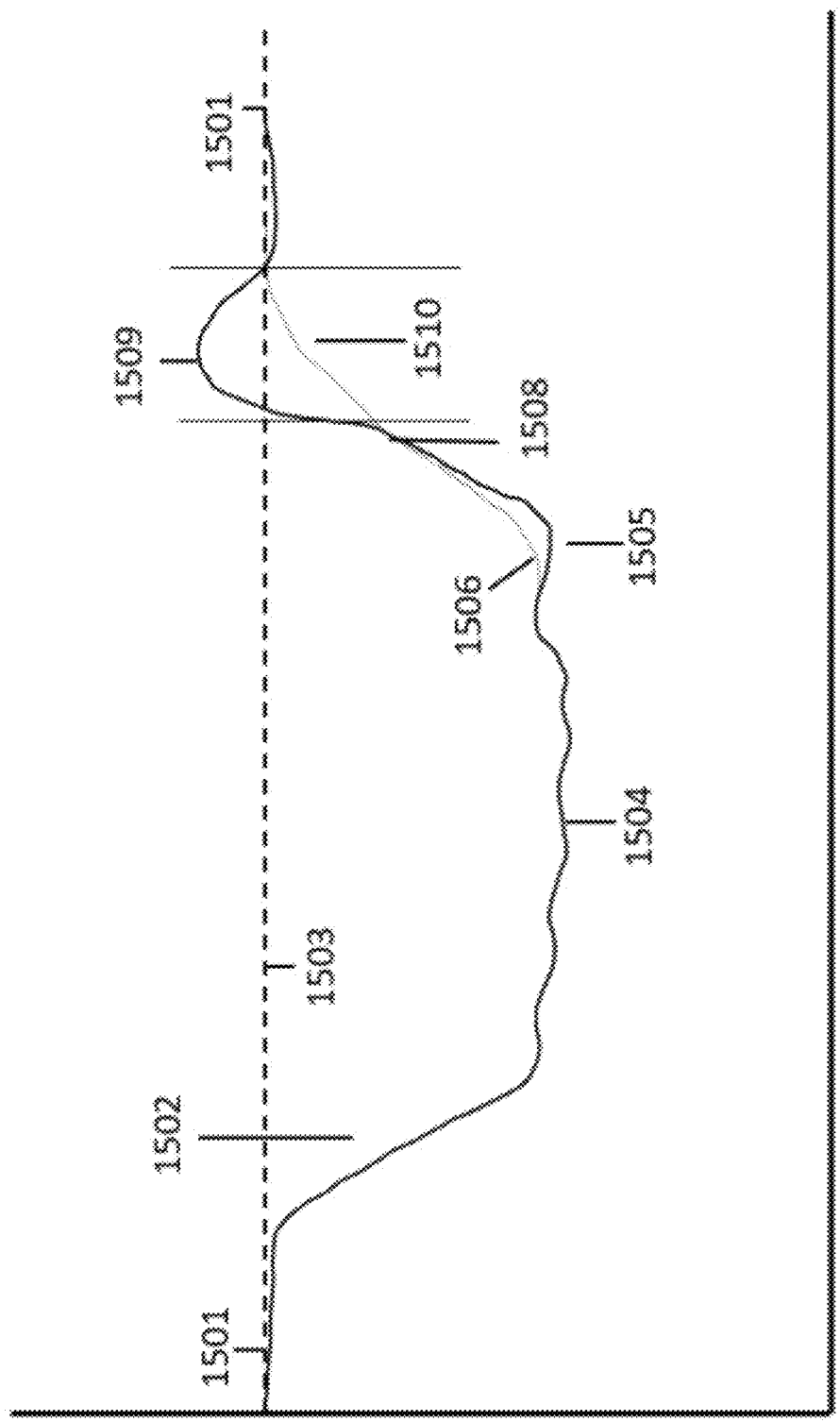
FIG. 15 is representing ABTT temperature measured in a user during a sleep cycle.

FIG. 15 shows a view of a conventional sleep curve and a sleep curve with awakening modified by the exemplary embodiment of the present disclosure. The conventional sleep curve 1505 is shown with a solid line, and the modified sleep curve 1506 is shown with a lighter line. A dashed horizontal line 1503 represents a typical core temperature, which is represented by the ABTT temperature, when awake. Awake is shown by 1501, transitioning to sleep 1502 is a user falling asleep, sleep 1504 shows a pattern of a user getting good rest. The pre-awakening 1508 is seen to be different for conventional sleep 1505 and modified sleep 1506, and the same can be said for transition to fully awake 1510. Overshoot 1509 temperature awakening only occurs during conventional sleep 1505.

In an unmodified or conventional awakening cycle 1505, core temperature spikes and an overshoot 1509 occurs, going above an awake temperature 1503 simultaneously with the release of adrenaline and related hormones. Pulse rate, blood pressure, and core temperature increase as the hypothalamus generates a condition that is akin in some respects to a "fight or flight" response. However, the hypothalamus, through millennia of evolution to survive in a hostile environment, initiates this wakening cycle as though wakening is to a threat. However, that threat typically no longer exists, so the awakening cycle causes undue stress on bodily organs, and can lead to stroke and/or heart attack. The systems of the present disclosure are designed to "trick" the hypothalamus into a modified response that subdues a normally rapid awakening to a modified awakening 1506 that involves a plurality of awakening stages that can include a plurality of temperature slopes and/or a plurality of different temperature curves.

In an exemplary example, the awakening process begins in a first stage approximately a half hour before awakening is desire. The systems of the present disclosure are initiated, causing a first, and gradual, change in core temperature that can last, for example for a first period, which can be, for example, approximately five minutes. Once the awakening process is started, a second phase of awakening can begin.

In the second phase of awakening, the awake state of the user is moved to a pre-awakening 1508 state by causing core body temperature to increase in a nearly linear curve. However, to prevent temperature over-spiking and undesirable adrenaline release, the slope of the curve in the modified awakening 1506 stage is decreased slightly near the end of this stage. Such decrease can be implemented by decreasing volume of sound, decreasing temperature, decreasing misting, decreasing light, etc. The purpose of decreasing stimulation is not to permit the user to return to a deeper sleep state, but to decrease the rate at which the user, who is not yet awake at the end of this stage, awakens. The second phase of awakening can extend, for example, for a period of approximately fifteen minutes.

In the third stage of awakening, the core or ABTT temperature curve is further modified by continuing to control the degree of stimulation, which is accomplished by decreasing or increasing the stimulation as needed to decrease the rate or slope of temperature increase as the user transitions from a light sleep to an awakened condition. Near the end of the transition stage the core or ABTT temperature curve flattens. The third stage can extend, for example, for an interval of five to ten minutes.

As the user awakens in the final, fourth stage, in which the core or ABTT temperature curve reaches the normal awake temperature 1501, stimulation can increase once again to complete the awakening process. This final stage can extend, for example from one to five minutes. However, since the transition is gradual and is from a lightly awakened state at the end of the third stage to a fully awakened state, temperature rises to the normal awake temperature rather than causing an overshoot 1509 of the normal awake temperature 1501. Thus, the systems and methods of the present disclosure function by initiating a plurality of artificially induced core or ABTT temperature curves including a plurality of slopes to reduce adrenaline release during awakening. It should be understood that since a response to awakening can be measured or characterized, precise measurement of core or ABTT temperature, while beneficial, may be replaced by a predetermined temperature control cycle that artificially induces the plurality of curves disclosed herein. It should be understood that the number of slopes can be infinite. However, as a practical matter, the number of curves is typically limited to 3 to 5 when a predetermined temperature cycle is used for control of the systems and methods disclosed herein. On the other hand, when core body temperature is measured, such as by ABTT terminus measurement, the temperature of the ABTT terminus 10 can be adjusted multiple times during awakening. Accordingly, the number of curves and/or slopes can be significant, for example, dozens, or more, when real time core temperature measurements are available.

It should be understood that the embodiments of FIGS. 4-14 can include input from ABTT sensors 303, as disclosed in FIG. 3. In addition, the at least one external ABTT processor and internal ABTT processor 102 can be positioned in the ABTT sensors 303, or in any other location, such as a cellphone, tablet, etc., rather than in a clock. Furthermore, though a clock is used as the location for some embodiments of the present disclosure, in other embodiments portions of the system can be positioned in or on a cellphone, tablet, and the like.

FIGS. 16-18 show the approximate location of these veins in relation to other facial features. The angular 20 and the facial 22 run up alongside a nose 26. The superior palpebral vein 16 runs along the eyebrow 28, The frontal vein 14 and the supraorbital vein 18 run through a forehead 30 and above the eye 31. For the purposes of this disclosure, terminology referring to relevant facial areas or veins herein will be described as one or more of the above-referenced veins, the ABTT terminus 10, the ABTT 12, and the brain core 24.

As described herein, veins 14, 16, 18, 20, and 22 converge in a superomedial orbit in a region of an upper eyelid and adjacent to the bridge of the nose, and flow directly, without inhibition, to the center of the brain. The skin in this area, as shown in the pending '421 application by the Applicant, is the thinnest skin in the body and free of fat, and by being in direct communication with the brain, the most direct path for measurement of a temperature of the brain. These vessels lack valves, which are typically an important barrier to flow and affect the accuracy of temperature measurement. Without valves, these blood vessels truly provide a direct, uninhibited passage for thermal messages from the hypothalamic region of the brain. The hypothalamic region of the brain is the link between a central nervous system and an endocrine system and, as such, acts as the center of control for basic bodily functions such as, for example, hunger, thirst, body temperature, fatigue, blood pressure, immune responses, circadian cycles, hormone production and secretion, and many others.

Figure 19:
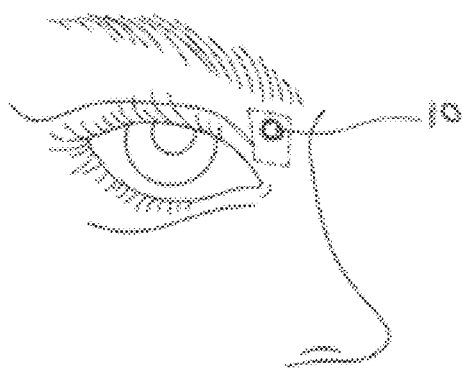
FIG. 19 shows the positioning of the ABTT on a human.
Figure 20:
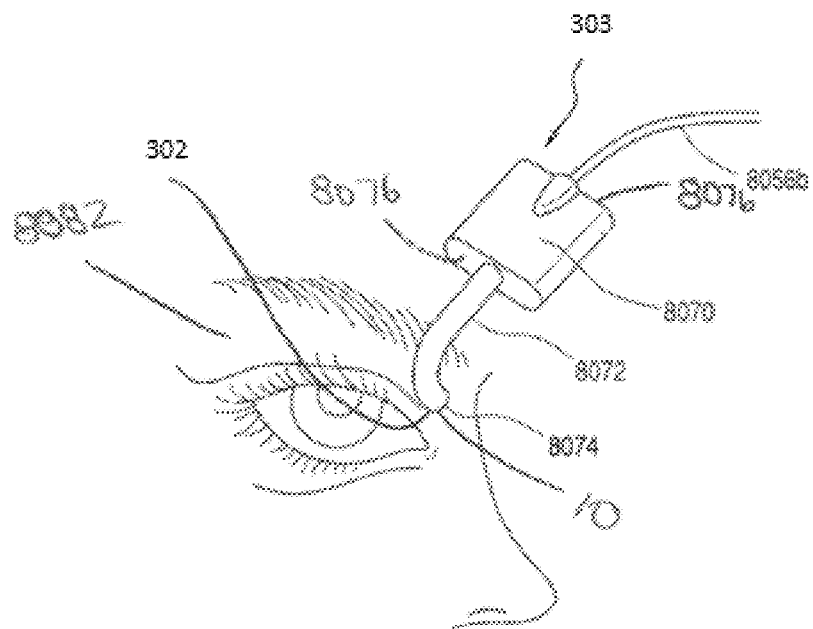
FIG. 20 shows a temperature modification device placed on the ABTT terminus of a human.

FIGS. 19 and 20 show a temperature sensor 303 and temperature modification device 302 in accordance with an exemplary embodiment of the present disclosure. The temperature sensor 303 temperature and modification device 303 is configured to have a supporting portion and an adhesive surface to be positioned on a forehead and retained in position with a suitable adhesive, a surgical tape, a head band, a hat, or other retention device such that the sensor and modification portion, described in more detail herein, is positioned on the skin adjacent to, over, or on the ABTT terminus 10. In addition to monitoring the temperature of ABTT terminus 10 with a temperature sensor 303, the system of the present disclosure can provide a heat to, and remove a heat from, the ABTT terminus 10 to encourage sleep The temperature sensor temperature modification device 303 is configured to be a device such as, for example, a thermoelectric device, a resistor based device, or an infrared device, that may be used for a continuous temperature monitoring, an intermittent temperature monitoring, and/or a thermal modification of ABTT terminus 10. The temperature sensor and the modification device 303 includes a plate-like or extended flat portion 8070, a curved finger portion 8072, and a probe 8074. The flat portion 8070 can include a temperature modification device, such as a thermoelectric device that can remove heat or generate heat. Probe 8074 can be a conductive material that couples the temperature modification device to the ABTT terminus 10. A probe 8074 can also include a temperature sensor 8080, such as a thermocouple, a thermistor, or other temperature sensing device.

In the exemplary embodiment of FIG. 20, a cable 8056*b* enters the flat portion 8070 from a first edge or side 8076 of the flat portion 8070, and the curved finger portion 8072 extends from a second, opposite edge or side 8076 from the first edge or side 8076 where the cable 8056*b* enters the flat portion 8070. The thermistor 8080 is positioned at an end of the finger 8072 that is opposite the end of the finger 8072 that extends from the second edge or side 8076. The finger 8072 may be flexible and movable into a plurality of positions to provide optimal contact to the probe 8074, including the temperature sensor 8080 and the user's ABTT 10. For use during sleep, the temperature sensor and the modification device 8004 may be retained on a face or the forehead 8082 by the adhesive, the surgical tape, a manual, or a mechanical retention, such as by an appliance, which may include a headband and hat.

In an exemplary embodiment the temperature sensor 302 and the temperature modification device 303 can also include an array, such as an infrared-sensitive array, and the array can automatically seek a highest or a peak temperature in the area of the ABTT terminus 10 once the temperature sensor 303 and temperature modification device 303 is positioned on the face or the forehead 8082, and the finger 8072 and the probe 8074 are positioned in proximity to, near to, alongside, adjacent, or close to the ABTT terminus 10. The sleep-facilitating processor can determine whether a located temperature is at or above a minimum predetermined temperature range indicative of the ABTT terminus 10. For example, a predetermined minimum temperature can be 98.0 Fahrenheit. However, the sleep system can be adjusted to set a lower predetermined temperature for hypothermic users, or for users in a sleep cycle where the temperature has decreased. Such decrease in the minimum predetermined temperature can be in a range of 1-3 degrees Celsius or in a range of 1.8-5.4 degrees Fahrenheit. For example, the predetermined minimum temperature can be 93.2 degrees Fahrenheit or 34 degrees Celsius, with a normal waking temperature of approximately 98.6 degrees Fahrenheit or 37 degrees Celsius.

The ability to monitor and add heat can enable the present system and apparatus to control the transition into sleep. More specifically, to transition into sleep the core temperature of the body declines from waking nominal to 2-3 degrees Celsius or 3.6-5.4 degrees Fahrenheit below waking nominal. The transition from waking to sleeping occurs over a time interval that is nominally 2.0 hours. However, there are variations between individuals, and the transition from waking temperature to sleeping temperature can be in a range of 1.5 to 2.5 hours. However, by manipulating heat removal from ABTT terminus by way of, for example, a thermoelectric cooler positioned in temperature sensor 303 and temperature modification device 302, the transition time from waking to sleeping can be manipulated. For example, in an exemplary embodiment, the transition from waking to sleeping can be manipulated by temperature sensor 303 temperature modification device 302 to be in a range of 1-3 hours. In another exemplary embodiment, the transition from waking to sleeping can be manipulated by temperature sensor/modification device 8004 to be in a range of 45 minutes to 3 hours. In yet another exemplary embodiment, the transition from waking to sleeping can be manipulated by temperature sensor 303 and temperature modification device 302 to be in a range of 30 minutes to 4 hours. The time of transition from a waking temperature to a sleeping temperature can be selected based on medical conditions. For example, a subject with a waking cycle based on initial sleep insertion might consistently awaken 3-5 hours after initial sleep. To increase the length of time of deeper sleep, temperature of ABTT terminus 10 can be artificially modified by temperature sensor 303 and temperature modification device 302 to decrease temperature in a period of about 30 minutes, promoting faster sleep and providing the subject with as much as 4.5 hours of deep sleep.

In another example, temperature regulation may cause some subjects to enter a depressed temperature cycle preparatory to sleep, but due to physiological problems, temperature fails to decrease to a temperature that induces full sleep and instead begins to climb, causing the subject to experience insomnia. In this situation, the system and apparatus of the present disclosure removes heat from ABTT terminus 10 to encourage a 2 hour transition from an awake temperature to a sleeping temperature, overcoming internal physiological control of core body temperature, as exemplified by temperature measurement of ABTT terminus 10.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by both this disclosure. It is indeed intended that the scope of this disclosure should be determined by a proper legal interpretation and construction of the disclosure, including equivalents, as understood by those of skill in the art relying upon the complete disclosure present at the time of fili

I claim:

1. A sleep enhancement system comprising: a temperature sensor configured to read a brain temperature signal of a sleeping user by way of an Abreu brain thermal tunnel (ABTT) terminus, the temperature sensor configured to transmit a signal corresponding to the brain temperature signal; at least one temperature modification device configured to be in direct or indirect contact with the user; a processor configured to receive the signal transmitted by the temperature sensor, to identify from the signal temperature over time to determine a temperature slope having an angle indicative of pre-awakening, and to send a signal to the at least one temperature modification device to decrease temperature applied to the user to suppress the slope angle of the temperature slope, wherein decreasing the temperature slope reduces temperature overshoot on awakening.

2. The sleep enhancement system of claim 1, wherein the temperature slope is a beginning of a shark fin and decreasing the temperature slope reduces a likelihood of transitioning into awakening.

3. The sleep enhancement system of claim 1, wherein the awakening of the user is enhanced by one or more of sound, misting, and light, and the processor decreases one or more of volume of the sound, amount of the misting, and intensity of the light to decrease a rate at which the user awakens.

4. The sleep enhancement system of claim 1, wherein vital signs of the user including one or more of a heart rate, an oxygen level, skin conductance, blood pressure, a respiration rate, body movement, a body position, and body sounds are monitored to provide additional information regarding a sleep state of the user.

5. The sleep enhancement system of claim 1, wherein the at least one temperature modification device includes a cooler, a heater, or a combination cooler and heater configured to be positioned on the ABTT terminus.

6. The sleep enhancement system of claim 1, wherein the at least one temperature modification device includes a cooler, a heater, or a combination cooler and heater configured to be applied to one or more extremities, a body, a head, or any combination of the one or more extremities, the body, and the head of the user.

7. A sleep enhancement system comprising: a temperature sensor configured to read a brain temperature signal of a user by way of an Abreu brain thermal tunnel (ABTT) terminus, the temperature sensor configured to transmit a signal corresponding to the brain temperature signal; at least one temperature modification device configured to be in direct or indirect contact with the user, the temperature modification device being a cooler, a heater, or a combination cooler and heater; a processor configured to receive the signal transmitted by the temperature sensor, to identify from the signal temperature over time to determine a temperature slope indicative of a transition to sleep, and after identifying the temperature slope indicative of the transition to sleep, to send a signal to the at least one temperature modification device to decrease temperature applied to the ABTT terminus of the user to enhance the transition to sleep.

8. The sleep enhancement system of claim 7, wherein the processor is configured to control one or more devices to enhance the transition to sleep by shutting the one or more devices down.

9. The sleep enhancement system of claim 8, wherein the one or more devices include at least one videogame, at least one communication device, at least one tablet, at least one cellphone, or at least one television.

10. The sleep enhancement system of claim 7, wherein the processor is configured to control one or more devices to enhance the transition to sleep, the one or more devices including blinds, curtains, or blinds and curtains, and the processor closes the blinds, the curtains, or the blinds and the curtains.

11. The sleep enhancement system of claim 7, wherein vital signs of the user including one or more of heart rate, oxygen level, skin conductance, blood pressure, respiration rate, body movement, body position, and body sounds are monitored to provide additional information regarding a sleep state of the user.

12. A sleep enhancement system comprising:
a temperature sensor configured to read a brain temperature signal of a user by way of an Abreu brain thermal tunnel (ABTT) terminus, the temperature sensor configured to transmit a signal corresponding to the brain temperature signal;
at least one temperature modification device configured to be in direct or indirect contact with the user;
a processor configured to receive the signal transmitted by the temperature sensor, the processor configured to:
identify from the signal temperature over time to determine a first temperature slope indicative of a transition to sleep, and control one or more devices to enhance the transition to sleep by controlling the first temperature slope, and
after identifying the transition to sleep, identifying from the signal temperature over time to determine a second temperature slope indicative of pre-awakening, and controlling the one or more devices to modify the second temperature slope to control a rate of pre-awakening to an awakened state.

13. The sleep enhancement system of claim 12, wherein the second temperature slope is a pre-awakening slope and modification of the second temperature slope is a suppression of the second temperature slope that reduces temperature overshoot on awakening.

14. The sleep enhancement system of claim 12, wherein the pre-awakening of the user is enhanced by one or more of sound, misting, and light, and the processor decreases one or more of volume of the sound, amount of the misting, and intensity of the light to decrease the rate at which the user awakens.

15. The sleep enhancement system of claim 12, wherein vital signs of the user include one or more of heart rate, oxygen level, skin conductance, blood pressure, respiration rate, body movement, body position, and body sounds are monitored by the processor to provide additional information regarding a sleep state of the user.

16. The sleep enhancement system of claim 12, wherein the at least one temperature modification device includes a cooler, a heater, or a combination cooler and heater configured to be positioned on the ABTT terminus.

17. The sleep enhancement system of claim 12, wherein the at least one temperature modification device includes a cooler, a heater, or a combination cooler and heater configured to be applied to one or more extremities, a body, a head, or any combination of the one or more extremities, the body, and the head of the user.

18. The sleep enhancement system of claim 12, wherein the processor is configured to control the one or more devices to enhance the transition to sleep by shutting the one or more devices down.

* * * * *